United States Patent
Enderling et al.

(10) Patent No.: US 12,406,772 B2
(45) Date of Patent: Sep. 2, 2025

(54) SYSTEMS AND METHODS FOR PREDICTING INDIVIDUAL PATIENT RESPONSE TO RADIOTHERAPY USING A DYNAMIC CARRYING CAPACITY MODEL

(71) Applicant: H. LEE MOFFITT CANCER CENTER AND RESEARCH INSTITUTE, INC., Tampa, FL (US)

(72) Inventors: Heiko Enderling, New Tampa, FL (US); Mohammad Zahid, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 353 days.

(21) Appl. No.: 17/786,326

(22) PCT Filed: Dec. 18, 2020

(86) PCT No.: PCT/US2020/065942
§ 371 (c)(1),
(2) Date: Jun. 16, 2022

(87) PCT Pub. No.: WO2021/127392
PCT Pub. Date: Jun. 24, 2021

(65) Prior Publication Data
US 2023/0038942 A1    Feb. 9, 2023

Related U.S. Application Data

(60) Provisional application No. 63/010,327, filed on Apr. 15, 2020, provisional application No. 62/950,296, filed on Dec. 19, 2019.

(51) Int. Cl.
*G16H 50/20* (2018.01)
*G06T 7/00* (2017.01)
(Continued)

(52) U.S. Cl.
CPC .......... *G16H 50/20* (2018.01); *G06T 7/0016* (2013.01); *G06T 7/62* (2017.01); *G16H 20/40* (2018.01);
(Continued)

(58) Field of Classification Search
CPC .......... A61N 5/103; G06T 2207/10081; G06T 2207/10088; G06T 2207/30096;
(Continued)

(56) References Cited

U.S. PATENT DOCUMENTS 8,768,431 B2 * 7/2014 Ross ................. A61B 5/415
382/128
11,491,350 B2 * 11/2022 Lou ................... G16H 50/70
(Continued)

OTHER PUBLICATIONS

Sotiris Prokopiou et al., "A proliferation saturation index to predict radiation response and personalize radiotherapy fractionation," Jul. 31, 2015, Radiation Oncology (2015) 10:159, pp. 1-6.*
(Continued)

*Primary Examiner* — Omar S Ismail
(74) *Attorney, Agent, or Firm* — Meunier Carlin & Curfman LLC

(57) ABSTRACT

Systems and methods for predicting outcome of radiation therapy is described herein. An example method includes receiving respective values for tumor volume of a target patients tumor at first and second time points, and calculating a change in tumor volume between the first and second time points. The method also includes estimating a patient-specific carrying capacity based on a logistic growth model and the change in tumor volume. Additionally, the method includes predicting a volume of the target patient's tumor at a future time point during radiation treatment based, at least in part, on a historical carrying capacity reduction fraction distribution and the patient-specific carrying capacity. The method further includes predicting a patient-specific out-
(Continued)

come of radiation therapy for the target patient based, at least in part, on the predicted volume of the target patients tumor at the future time point.

18 Claims, 21 Drawing Sheets

(51) Int. Cl.
  *G06T 7/62* (2017.01)
  *G16H 20/40* (2018.01)
(52) U.S. Cl.
  CPC ............ *G06T 2207/10081* (2013.01); *G06T 2207/10088* (2013.01); *G06T 2207/30096* (2013.01)
(58) Field of Classification Search
  CPC ......... G06T 7/0016; G06T 7/62; G16H 20/40; G16H 30/40; G16H 50/20
  See application file for complete search history.

(56) References Cited

U.S. PATENT DOCUMENTS

| | | | | |
|---|---|---|---|---|
| 2003/0235816 | A1* | 12/2003 | Slawin | G01N 33/57434 435/5 |
| 2008/0299123 | A1* | 12/2008 | Altevogt | A61P 35/00 530/387.5 |
| 2009/0053244 | A1* | 2/2009 | Chen | A61K 31/7068 435/235.1 |
| 2010/0135903 | A1* | 6/2010 | Brown | A61K 31/7068 424/1.61 |
| 2011/0103657 | A1* | 5/2011 | Kang | G06T 7/20 382/128 |
| 2013/0004044 | A1* | 1/2013 | Ross | G06T 7/0016 382/128 |
| 2014/0271818 | A1* | 9/2014 | James | C12N 15/1138 435/320.1 |
| 2015/0056144 | A1* | 2/2015 | Aboody | A61K 49/085 424/9.32 |
| 2016/0239956 | A1* | 8/2016 | Kang | A61B 6/5247 |
| 2016/0266126 | A1* | 9/2016 | Shipitsin | G06T 7/11 |
| 2016/0333083 | A1* | 11/2016 | James | C07K 16/3023 |
| 2017/0106213 | A1* | 4/2017 | Lee | A61B 6/032 |
| 2017/0150934 | A1* | 6/2017 | Bennett | A61N 5/1077 |
| 2017/0209715 | A1* | 7/2017 | Ruebel | A61N 5/1067 |
| 2017/0216632 | A1* | 8/2017 | Lee | A61N 5/1049 |
| 2017/0309025 | A1* | 10/2017 | O'Rourke | G06T 7/0012 |
| 2017/0348547 | A1* | 12/2017 | Lee | A61N 5/1037 |
| 2018/0012727 | A1* | 1/2018 | Amato | A61B 6/4035 |
| 2018/0078790 | A1* | 3/2018 | Lee | G21K 5/10 |
| 2018/0092968 | A1* | 4/2018 | Albelda | C07K 14/705 |
| 2018/0185673 | A1* | 7/2018 | Lee | G21K 1/093 |
| 2018/0298068 | A1* | 10/2018 | Albelda | A61K 39/001182 |
| 2018/0318605 | A1* | 11/2018 | Da Silva Rodrigues | A61N 5/1049 |
| 2018/0326223 | A1* | 11/2018 | Willcut | A61N 5/1039 |
| 2019/0021684 | A1* | 1/2019 | Ruebel | A61N 5/1082 |
| 2019/0114765 | A1* | 4/2019 | Enderling | G16H 30/20 |
| 2019/0201717 | A1* | 7/2019 | Shangguan | A61N 5/1071 |
| 2020/0390811 | A1* | 12/2020 | Albelda | A61K 40/31 |
| 2021/0164056 | A1* | 6/2021 | Spiotto | G01N 33/57415 |
| 2022/0016169 | A1* | 1/2022 | Hong | A61K 40/42 |

OTHER PUBLICATIONS

Sebastien Benzekry et al., "Classical Mathematical Models for Description and Prediction of Experimental Tumor Growth," Aug. 28, 2014, PLOS Coputational Biology, vol. 10, Issue 8,e1003800, pp. 1-17.*

Maxwell Lewis Neal et al., "Discriminating Survival Outcomes in Patients with Glioblastoma Using a Simulation-Based, Patient-Specific Response Metric, "Jan. 23, 2013,PLOS ONE, Jan. 2013 Vol.,Issue 1, e51951, pp. 1-5.*

Imran Tariq et al., "Mathematical modelling of tumour volume dynamics in response to stereotactic ablative radiotherapy for non-small cell lung cancer, "Apr. 17, 2015,Physics in Medicine & Biology,60 (2015) 3695, pp. 3695-3710.*

Jan Poleszczuk et al., "Predicting Patient-Specific Radiotherapy Protocols Based on Mathematical Model Choice for Proliferation Saturation Index," Jul. 5, 2017,Society for Mathematical Biology 2017, pp. 1195-1204.*

Enakshi D. Sunassee et al., "Proliferation saturation index in an adaptive Bayesian approach to predict patient-specific radiotherapy responses, "Mar. 19, 2019,International Journal of Radiation Biology, pp. 1421-1425.*

Heiko Enderling et al., "Quantitative Modeling of Tumor Dynamics and Radiotherapy,"Jul. 24, 2010,Acta Biotheor (2010) 58, pp. 341-350.*

International Search Report and Written Opinion in PCT/US2020/065942. Mailed Mar. 23, 2021. 9 pages.

* cited by examiner

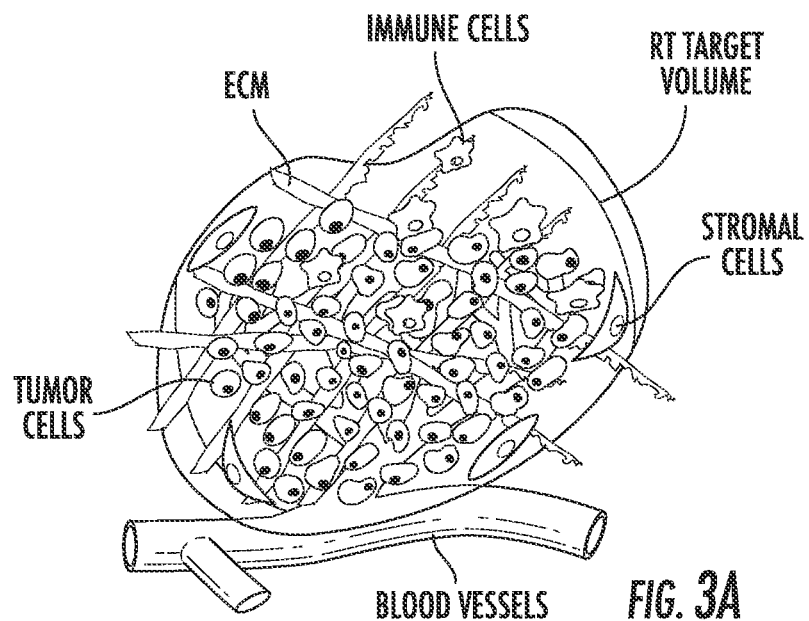
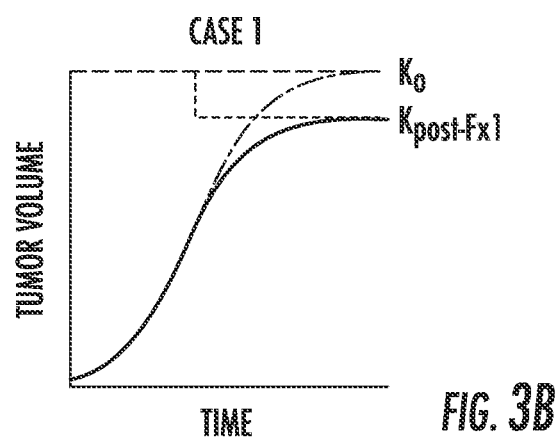
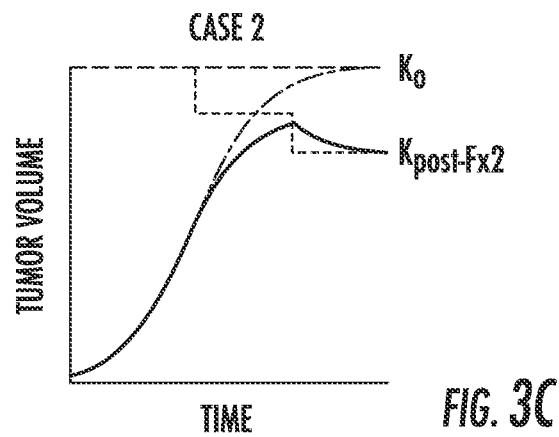

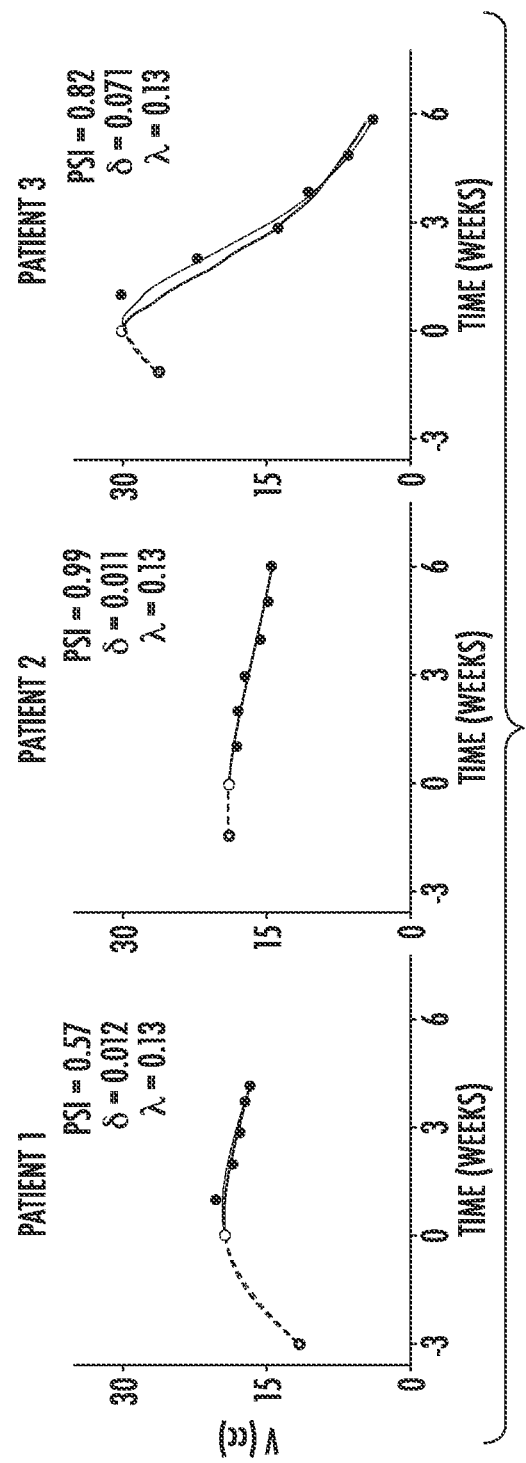
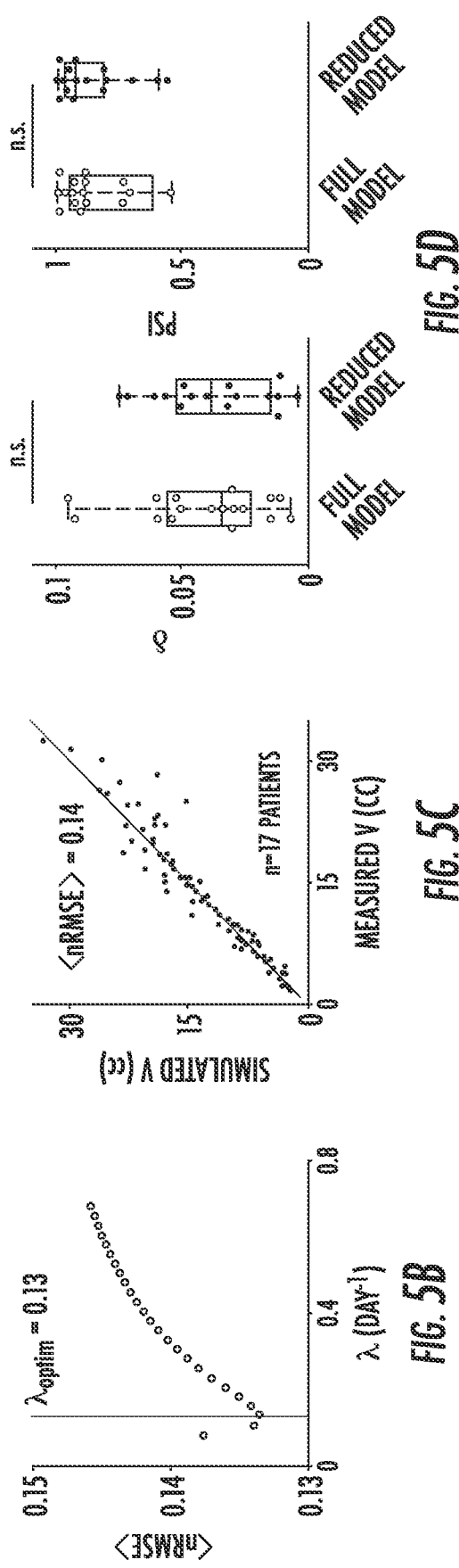
FIG. 5A
FIG. 5B
FIG. 5C
FIG. 5D

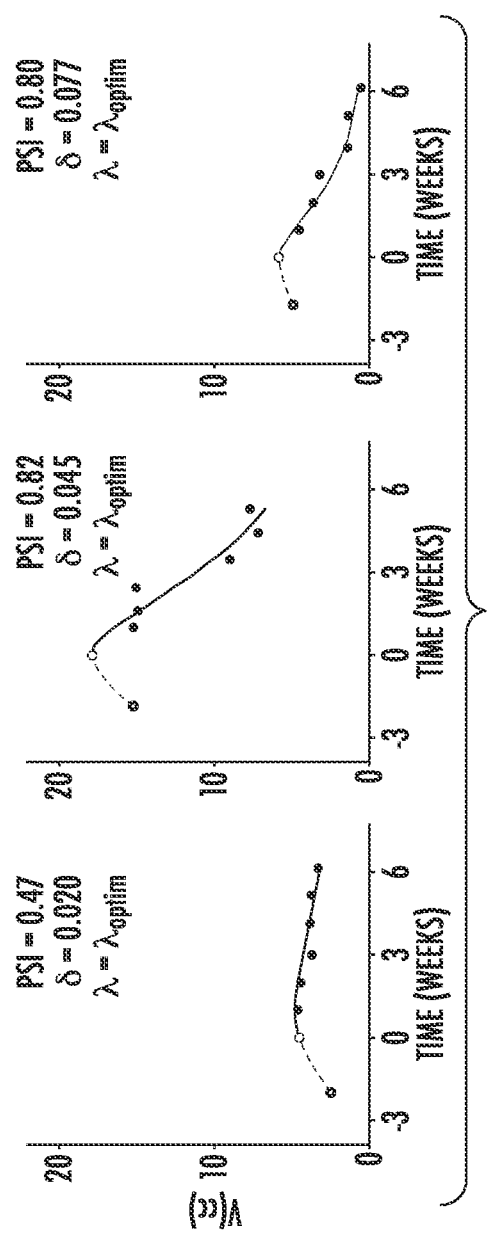
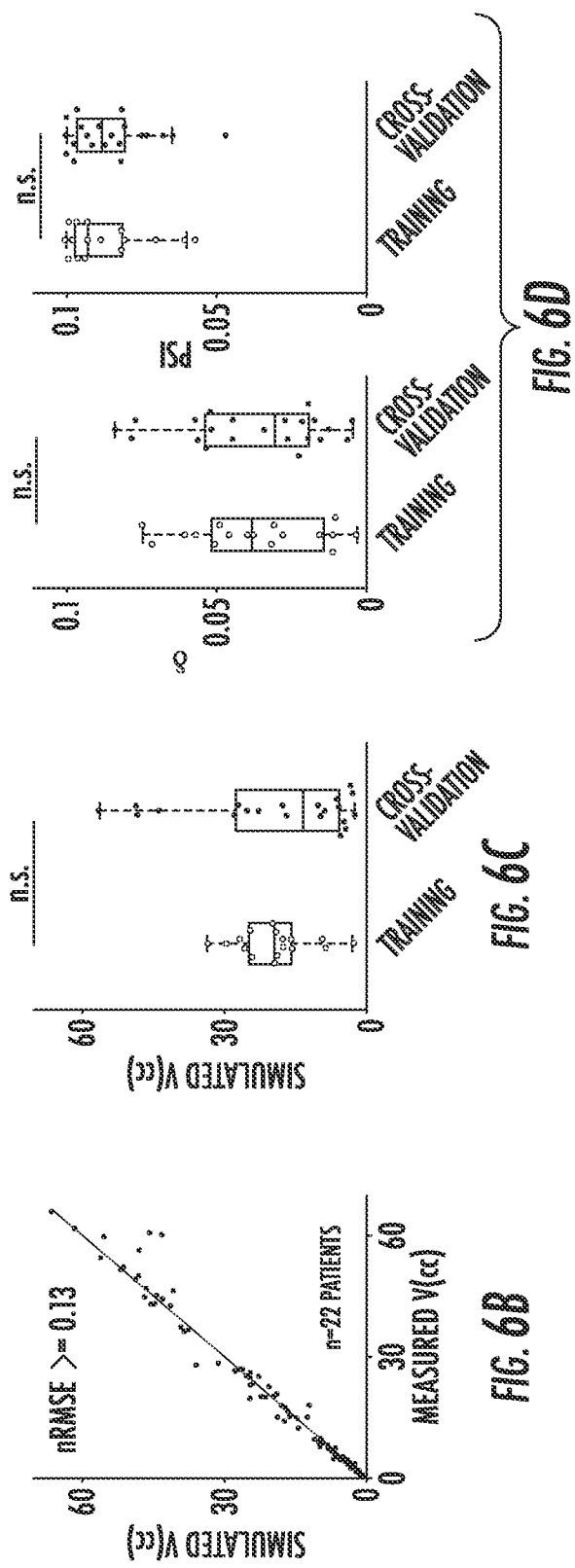
FIG. 6A
FIG. 6B
FIG. 6C
FIG. 6D

|  | Training Cohort, n = 17 (MCC) | Validation Cohort, n = 22 (MDACC) |  |
|---|---|---|---|
| Primary Site | n (%) | | |
| Bilateral | 1 (5.9%) | 0 (0%) | 0.44 |
| Base of tongue | 0 (0%) | 8 (36.4%) | 0.0056 |
| Gum | 0 (0%) | 1 (4.6%) | 1.0 |
| Oral cavity | 2 (11.8%) | 0 (0%) | 0.18 |
| Oropharynx | 14 (82.4%) | 0 (0%) | $4.5 \times 10^{-8}$ |
| Soft palate | 0 (0%) | 1 (4.6%) | 1.0 |
| Tongue | 0 (0%) | 2 (9.1%) | 0.50 |
| Tonsil | 0 (0%) | 10 (45.5%) | 0.0019 |
| T stage | | | |
| T1 | 3 (17.7%) | 7 (31.8%) | 0.46 |
| T2 | 8 (47.1%) | 8 (36.4%) | 0.53 |
| T3 | 4 (23.5%) | 2 (9.1%) | 0.37 |
| T4 | 0 (0%) | 5 (22.7%) | 0.057 |
| TX | 2 (11.8%) | 0 (0%) | 0.18 |
| N stage | | | |
| N0 | 1 (5.9%) | 0 (0%) | 0.44 |
| N1 | 1 (5.9%) | 2 (9.1%) | 1.0 |
| N2 | 13 (76.5%) | 20 (90.9%) | 0.37 |
| Metastases? | | | |
| No | 17 (100.0%) | 22 (100.0%) | 1.0 |
| Yes | 0 (0%) | 0 (0%) | 1.0 |
| Treatment | | | |
| RT alone | 0 (0%) | 11 (50.0%) | $6.8 \times 10^{-4}$ |
| Chemo + RT | 17 (100.0%) | 11 (50.0%) | $6.8 \times 10^{-4}$ |
| p16 status | | | |
| Positive | 6 (35.3%) | 16 (72.7%) | 0.026 |
| Negative | 5 (29.4%) | 5 (22.7%) | 0.72 |
| Unknown | 6 (35.3%) | 1 (4.6%) | 0.03 |

FIG. 9

| Uniform Parameter s | Free Parameters, p | $R^2$ | Average AIC $2p + n\ln(\Sigma SSE)$ | Average BIC $p\ln(n) + n\ln\left(\Sigma\frac{SSE}{n}\right)$ |
|---|---|---|---|---|
| $\lambda$ | 1 | .925 | 13.60 | 3.08 |
| $\delta$ | 1 | .673 | 22.55 | 12.04 |
| $\lambda, \delta$ | 0 | .888 | 21.58 | 11.30 |

*FIG. 10*

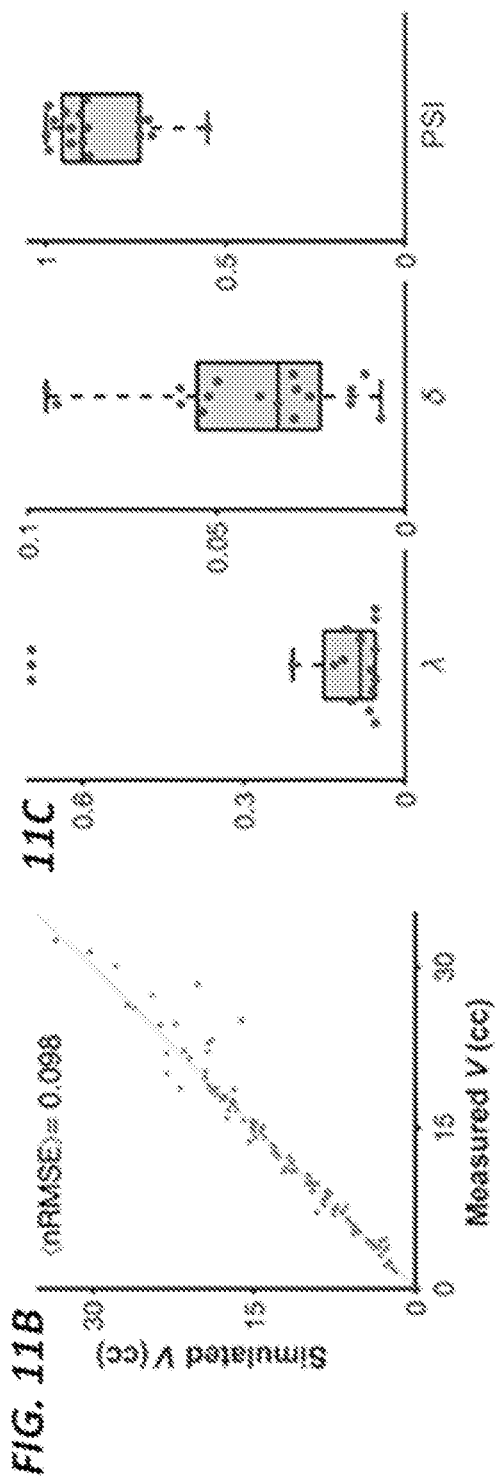

SYSTEMS AND METHODS FOR PREDICTING INDIVIDUAL PATIENT RESPONSE TO RADIOTHERAPY USING A DYNAMIC CARRYING CAPACITY MODEL

CROSS REFERENCE TO RELATED APPLICATIONS

This application is a United States National Phase Patent Application of International Patent Application Number PCT/US2020/065942, filed on Dec. 18, 2020, which claims the benefit of U.S. provisional patent application No. 62/950,296, filed on Dec. 19, 2019, and titled "Proliferation Saturation Index in an adaptive Bayesian approach to predict patient-specific radiotherapy responses," and U.S. provisional patent application No. 63/010,327, filed on Apr. 15, 2020, and titled "SYSTEMS AND METHODS FOR PREDICTING INDIVIDUAL PATIENT RESPONSE TO RADIOTHERAPY USING A DYNAMIC CARRYING CAPACITY MODEL," the disclosures of which are expressly incorporated herein by reference in their entireties.

BACKGROUND

Radiation therapy (RT) is the single most utilized therapeutic agent in oncology[1,2]. While the flood of genomic data has thus far affected chemotherapy and certain targeted biological agents, it has yet to impact RT. With increasing understanding of the complexity of tumor heterogeneity, the central principle underlying precision medicine calls for cancer therapy to be tailored to individual patients. To this effect, actionable biomarkers need to be identified that adequately describe individual patients' tumor growth dynamics and therapy responses. It was recently postulated that the future of personalized radiation therapy will need to integrate and synergize clinical radiation oncology with the expertise of molecular biology, immunology, radiomics, and mathematical modeling[3-5].

In vivo radiation sensitivity has been described in terms of a 10-gene molecular signature, and this genomic indicator has been shown to be highly heterogeneous within and between different cancer types[6-8]. The prevailing dogma in mathematical modeling of radiotherapy of the major effect of radiation remains DNA damage-induced direct cell death, and treatment schedules are derived to maximize tumor control probability while minimizing normal tissue complication probability[2,9]. The Linear-Quadratic (LQ) model is the gold standard to describe the in vitro radiosensitivity of cells[10-12]. Indeed, most—if not all—quantitative modeling studies use the LQ-model-derived dose-dependent survival fraction to calibrate radiotherapy cell death rates[13]. To account for non-direct cell killing effects of radiation, recent developments of the LQ-model include radiation bystander effects[14].

Cell intrinsic radiation sensitivity, however, has recently been argued to be less of a factor than patient-specific tumor-microenvironmental properties that modulate the fraction of actively proliferating cells in a tumor. The proliferation saturation index (PSI) describes the ratio of the tumor volume prior to radiation to its pre-irradiation carrying capacity—the maximum tumor volume that can be supported by the host tissue[15,16]. PSI ranges between 0 and 1, where when PSI=0 the entire tumor volume is considered as proliferative and tumor growth is purely exponential, and when PSI=1 the entire tumor volume is considered as non-proliferative with zero tumor growth. Tumor dormancy is a visualization of tumors at carrying capacity. Notably, carrying capacity and PSI are emergent properties of multiple factors. Model analysis has shown that PSI can better describe clinically observed volumetric regression during RT than any single measure of radiosensitivity[15,17]. Although PSI offers a conceptual departure from traditional radiation modeling, it so far has continued to rely on an explicit radiation-induced cell death term.

In recent years, cancer biology has shifted from a cell-centric view toward an integrated view of the tumor ecosystem[18-21]. As such, the effect of radiation on different tumor microenvironment components has become of increasing interest[22]. An extensive body of literature has emerged relating to the immune-activating ability of RT[23-27]. In fact, RT efficacy may be a combination of the cytotoxic effect of radiation on cancer cells and the direct and indirect effects on the complex tumor microenvironment within the radiation treatment field. Radiation alters the tumor vasculature[28] and releases tumor-specific antigens damage-associated molecular patterns that stimulate subsequent anti-tumor immunity[29]—all of which may change the tumor carrying capacity.

SUMMARY

An example method for predicting response to and/or outcome of radiation therapy is described herein. The method includes receiving respective values for tumor volume of a target patient's tumor at a first time point and a second time point, calculating a change in tumor volume between the first and second time points based on the respective values for tumor volume, and estimating a patient-specific carrying capacity based on a logistic growth model and the change in tumor volume between the first and second time points. The method also includes predicting a volume of the target patient's tumor at a future time point during radiation treatment based, at least in part, on a historical carrying capacity reduction fraction distribution and the patient-specific carrying capacity. The method further includes predicting a patient-specific outcome of radiation therapy for the target patient based, at least in part, on the predicted volume of the target patient's tumor at the future time point.

Additionally, the first point in time is prior to a beginning of radiation therapy, and the second point in time is at a beginning of radiation treatment.

Alternatively or additionally, the method optionally further includes receiving a respective value for tumor volume of the target patient's tumor at a third time point; calculating a change in tumor volume between the second and third time points based on the respective values for tumor volume; estimating a patient-specific carrying capacity reduction fraction based on the logistic growth model and the change in tumor volume between the second and third time points; and predicting the volume of the target patient's tumor at the future time point during radiation treatment based, at least in part, on the patient-specific carrying capacity reduction fraction and the change in tumor volume between the second and third time points. The third time point is during administration of radiation treatment. For example, the third time point is at a second, third, fourth, or fifth week of radiation treatment. Alternatively or additionally, the future time point is at a sixth week of radiation treatment.

In some implementations, the step of predicting the volume of the target patient's tumor at the future time point in radiation treatment based, at least in part, on the patient-specific carrying capacity reduction fraction and the change in tumor volume between the second and third time points includes updating the historical carrying capacity reduction fraction distribution to include the patient-specific carrying capacity reduction fraction for the target patient; randomly sampling from the updated historical carrying capacity reduction fraction distribution; and simulating tumor volume dynamics during radiation treatment for the target patient.

In some implementations, the method optionally further includes weighting the patient-specific carrying capacity reduction fraction for the target patient.

In some implementations, the patient-specific outcome is predicted by comparing a change in tumor volume at the future time point to a threshold.

In some implementations, the predicted patient-specific outcome is locoregional control (LRC).

In some implementations, the predicted patient-specific outcome is disease-free survival (DFS).

In some implementations, the predicted patient-specific outcome is a percentage chance of success of radiation therapy.

In some implementations, the method optionally further includes receiving at least two images of the patient's tumor, where a first image is captured at the first time point and a second image is captured at the second time point; and deriving the respective values for tumor volume at the first and second time points from the first and second images, respectively.

In some implementations, the at least two images are computed-tomography (CT) images.

In some implementations, the at least two images are magnetic resonance images (MRI).

In some implementations, the method optionally further includes treating the target patient based on the predicted patient-specific outcome.

In some implementations, the method optionally further includes administering radiation treatment after the second time point.

In some implementations, the target patient's tumor is head and neck cancer.

An example system for predicting response to and/or outcome of radiation therapy is also described herein. The system includes a processor and a memory having computer-executable instructions stored thereon. The processor is configured to receive respective values for tumor volume of a target patient's tumor at a first time point and a second time point, calculate a change in tumor volume between the first and second time points based on the respective values for tumor volume, and estimate a patient-specific carrying capacity based on a logistic growth model and the change in tumor volume between the first and second time points. The processor is also configured to predict a volume of the target patient's tumor at a future time point during radiation treatment based, at least in part, on a historical carrying capacity reduction fraction distribution and the patient-specific carrying capacity. The processor is further configured to predict a patient-specific outcome of radiation therapy for the target patient based, at least in part, on the predicted volume of the target patient's tumor at the future time point Additionally, the first point in time is prior to a beginning of radiation therapy, and the second point in time is at a beginning of radiation treatment.

Alternatively or additionally, the processor is optionally further configured to receive a respective value for tumor volume of the target patient's tumor at a third time point; calculate a change in tumor volume between the second and third time points based on the respective values for tumor volume; estimate a patient-specific carrying capacity reduction fraction based on the logistic growth model and the change in tumor volume between the second and third time points; and predict the volume of the target patient's tumor at the future time point during radiation treatment based, at least in part, on the patient-specific carrying capacity reduction fraction and the change in tumor volume between the second and third time points. The third time point is during administration of radiation treatment. For example, the third time point is at a second, third, fourth, or fifth week of radiation treatment. Alternatively or additionally, the future time point is at a sixth week of radiation treatment.

In some implementations, the step of predicting the volume of the target patient's tumor at the future time point in radiation treatment based, at least in part, on the patient-specific carrying capacity reduction fraction and the change in tumor volume between the second and third time points includes updating the historical carrying capacity reduction fraction distribution to include the patient-specific carrying capacity reduction fraction for the target patient; randomly sampling from the updated historical carrying capacity reduction fraction distribution; and simulating tumor volume dynamics during radiation treatment for the target patient.

In some implementations, the processor is optionally further configured to weight the patient-specific carrying capacity reduction fraction for the target patient.

In some implementations, the patient-specific outcome is predicted by comparing a change in tumor volume at the future time point to a threshold.

In some implementations, the predicted patient-specific outcome is locoregional control (LRC).

In some implementations, the predicted patient-specific outcome is disease-free survival (DFS).

In some implementations, the predicted patient-specific outcome is a percentage chance of success of radiation therapy.

In some implementations, the processor is optionally further configured to receive at least two images of the patient's tumor, where a first image is captured at the first time point and a second image is captured at the second time point; and derive the respective values for tumor volume at the first and second time points from the first and second images, respectively.

In some implementations, the at least two images are computed-tomography (CT) images.

In some implementations, the at least two images are magnetic resonance images (MRI).

In some implementations, the target patient's tumor is head and neck cancer.

Another example method for predicting response to and/or outcome of radiation therapy is described herein. The method includes receiving respective values for tumor volume of a target patient's tumor for at least two time points, calculating a change in tumor volume between the at least two time points based on the respective values for tumor volume, and estimating a patient-specific carrying capacity reduction fraction based on a logistic growth model and the change in tumor volume between the at least two time points. The method also includes predicting a volume of the target patient's tumor at a future time point during radiation treatment based, at least in part, on the patient-specific carrying capacity reduction fraction and the change in tumor volume between the at least two time points. The method further includes predicting a patient-specific outcome of radiation therapy for the target patient based, at least in part, on the predicted volume of the target patient's tumor at the future time point, wherein the at least two time points include a beginning of radiation treatment and a time point during radiation treatment.

Additionally, the time point during radiation treatment is at a second, third, fourth, or fifth week of radiation treatment. Alternatively or additionally, the future time point is at a sixth week of radiation treatment.

Another example system for predicting response to and/or outcome of radiation therapy is described herein. The system includes a processor and a memory having computer-executable instructions stored thereon. The processor is configured to receive respective values for tumor volume of a target patient's tumor for at least two time points, calculate a change in tumor volume between the at least two time points based on the respective values for tumor volume, and estimate a patient-specific carrying capacity reduction fraction based on a logistic growth model and the change in tumor volume between the at least two time points. The processor is also configured to predict a volume of the target patient's tumor at a future time point during radiation treatment based, at least in part, on the patient-specific carrying capacity reduction fraction and the change in tumor volume between the at least two time points. The processor is further configured to predict a patient-specific outcome of radiation therapy for the target patient based, at least in part, on the predicted volume of the target patient's tumor at the future time point. The at least two time points include a beginning of radiation treatment and a time point during radiation treatment.

Additionally, the time point during radiation treatment is at a second, third, fourth, or fifth week of radiation treatment. Alternatively or additionally, the future time point is at a sixth week of radiation treatment.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 3A-3C show radiation-induced reduction of carrying capacity. FIG. 3A is a schematic showing how a RT target volume encompasses both the tumor and the tumor microenvironment which includes extracellular matrix (ECM), immune cells, stromal cells, and vasculature. In FIGS. 3B and 3C, tumor growth is modeled as logistic growth and the effect of RT is modeled as an instantaneous reduction in the carrying capacity leading to two cases: slowed tumor growth when the reduced carrying remains larger than the current tumor volume (FIG. 3B) or tumor volume reduction when the reduced carrying capacity drops below the current tumor volume. In this case, the tumor volume will subsequently approach the carrying capacity from above. (FIG. 3C). In FIGS. 3B and 3C, the orange dashed line indicates the carrying capacity before RT ($K_o$), the green dash-dot curve indicates the trajectory the tumor volume would have followed without RT, the red dashed line indicates how the carrying capacity changes in response to RT, and solid blue curves indicate the tumor volume trajectories after RT.

FIGS. 5A-5D show model fit results for training cohort with uniform A and patient-specific δ values. FIG. 5A is representative fitting results for three patients demonstrating the rich variety of response dynamics that the model can capture. Magenta curves (dashed for pre-treatment calculations and solid for on-treatment fits) show volume trajectories from the full model with patient-specific A values; blue curves (dashed for pre-treatment calculations and solid for on-treatment fits) show volume trajectories from the reduced model using $\lambda_{optim}=0.13$ day$^{-1}$ across all patients. FIG. 5B illustrates finding optimal A to minimize average normalized root mean square error (nRMSE) for the training cohort. FIG. 5C illustrates correlation of simulated volumes for the reduced model to the measured tumor volumes for all 17 patients in the training cohort. FIG. 5D illustrates parameter distributions across all patients for both the full model and the reduced model (median and interquartile divisions indicated).

FIGS. 6A-6D show model fit results for cross-validation cohort with uniform A learned from training cohort and patient-specific δ values. FIG. 6A illustrate representative fitting results for three patients demonstrating the rich variety of response dynamics that the model can capture. Volume trajectories are from the reduced model using $\lambda_{optim}$ learned from the training cohort for all patients. FIG. 6B illustrates correlation of simulated volumes to the measured tumor volumes for all 22 patients in the cross-validation cohort. FIG. 6C illustrates box plots comparing tumor volumes at the start of RT of the training cohort (n=17 patients) and the cross-validation cohort (n=22 patients). FIG. 6D illustrates box plots showing parameter distributions across all patients comparing the results from the training and cross-validation cohorts. For each box plot, median and interquartile divisions are indicated.

FIG. 7A illustrates scatter plot of δ and the weekly percent volume reduction with all 39 quadratic fits from the leave-one-out analyses overlaid that serves as S estimator derived from each corresponding training cohort. FIG. 7B illustrates histograms of the fitted values for S for each leave-one-out training cohort, which serves as chosen training δ-distribution, with a uniform $\lambda=0.13$ day$^{-1}$ with lognormal fits to the distribution overlaid. FIG. 7C illustrates plot showing the ranges for the LRC and DFS prediction cutoffs derived from the 39 leave-one-out training cohorts. Error bars indicate standard deviations across the 39 training cohorts. FIG. 7D illustrates Kaplan-Meier analysis for LRC and DFS for the 39 leave-one-out training cohorts separated by their respective percent volume reduction threshold after 6 weeks of RT. FIG. 7E illustrates representative spaghetti plots of tumor volume prediction simulations. 100 prediction simulations for patient 10 for $n_{meas}$=0-4. Light green circles around the black dots indicate measurements that were considered in making predictions. FIG. 7F illustrates results of 100 prediction simulations from the leave-one-out analyses showing the predicted normalized tumor volumes at the sixth week on RT (colored dots) compared to the measured normalized tumor volume (black asterisks). In FIGS. 7E-7F, black dashed lines indicate the patient-specific cutoffs for LRC prediction; the cyan dashed lines indicate the patient-specific cutoffs for DFS prediction. Blank columns indicate that predictions were not made for patients that did not have a volume measurement at week 6; red diamonds indicate simulations with estimated volumes outside of the displayed area.

FIG. 8A illustrates receiver operator characteristic (ROC) plots summarizing the pipeline results from the 39 leave-one-out studies to predict LRC and DFS for each left-out patient with increasing number of weekly measurements being considered. Each marker shows the performance of 10 simulations of 500 predictions each; the gray unit line indicates the chance line in the ROC space. FIG. 8B illustrates ROC curves for predicting LRC and DFS using volume reduction relative to start of RT from for weeks 1-6 of RT. FIG. 8C illustrates comparison of Youden's J-statistic for the model predictions (teal) and predictions using volume reduction alone (black) compared information available at different weeks of RT.

FIG. 9 is Table 1, which shows patient characteristics for training and validation cohorts.

FIG. 10 is Table 2, which shows Parameter Reduction Analysis.

FIGS. 11A-11C show model fit results for training cohort with patient specific and δ values. FIG. 11A illustrates representative fitting results for three patients demonstrating the rich variety of response dynamics that the model can capture. The red dots indicate tumor volume at the time of treatment planning; green dots indicate tumor volumes at the start of RT; black dots indicate weekly tumor volumes during RT; blue dashed curves are the pre-treatment volume trajectories ($V_{pre-RT}$) calculated from 2 pre-treatment measurements; blue curves are the model fits for on-treatment volume trajectories ($V_{on-RT}$); red dashed are the tumor carrying capacity. FIG. 11B illustrates correlation of simulated volumes to the measured tumor volumes for all 17 patients. Red dots indicate individual weekly time points. The normalized root mean square error (nRMSE) value shows the average error per patient between the simulated and measured volumes and thus the accuracy of the simulations. FIG. 11C illustrates box plots showing parameter distributions across all patients (median and interquartile divisions indicated and whiskers maximally extend to 1.5 times the interquartile range).

FIG. 14A illustrates volume trajectories for the 14 patients with tumor volumes less than 30 cc. FIG. 14B illustrates volume trajectories for the 5 patients with tumor volumes greater than 30 cc.

FIG. 15A illustrates scatter plot of 6 and the volume at the start of RT for the MCC testing cohort. FIG. 15B illustrates scatter plot of 6 and proliferation saturation index for the MCC testing cohort.

FIG. 16A illustrates plots of sensitivity values for 20-500 prediction simulations, for $n_{meas}$=1-4. Error bars indicate the standard error of the mean; horizontal black lines indicate the mean value for 500 predictions. FIG. 16B illustrates plots of (1-specificity) values for 20-500 prediction simulations, for $n_{meas}$=1-4. Error bars indicate the standard error of the mean; horizontal black lines indicate the mean value for 500 predictions.

DETAILED DESCRIPTION

Figure 1:
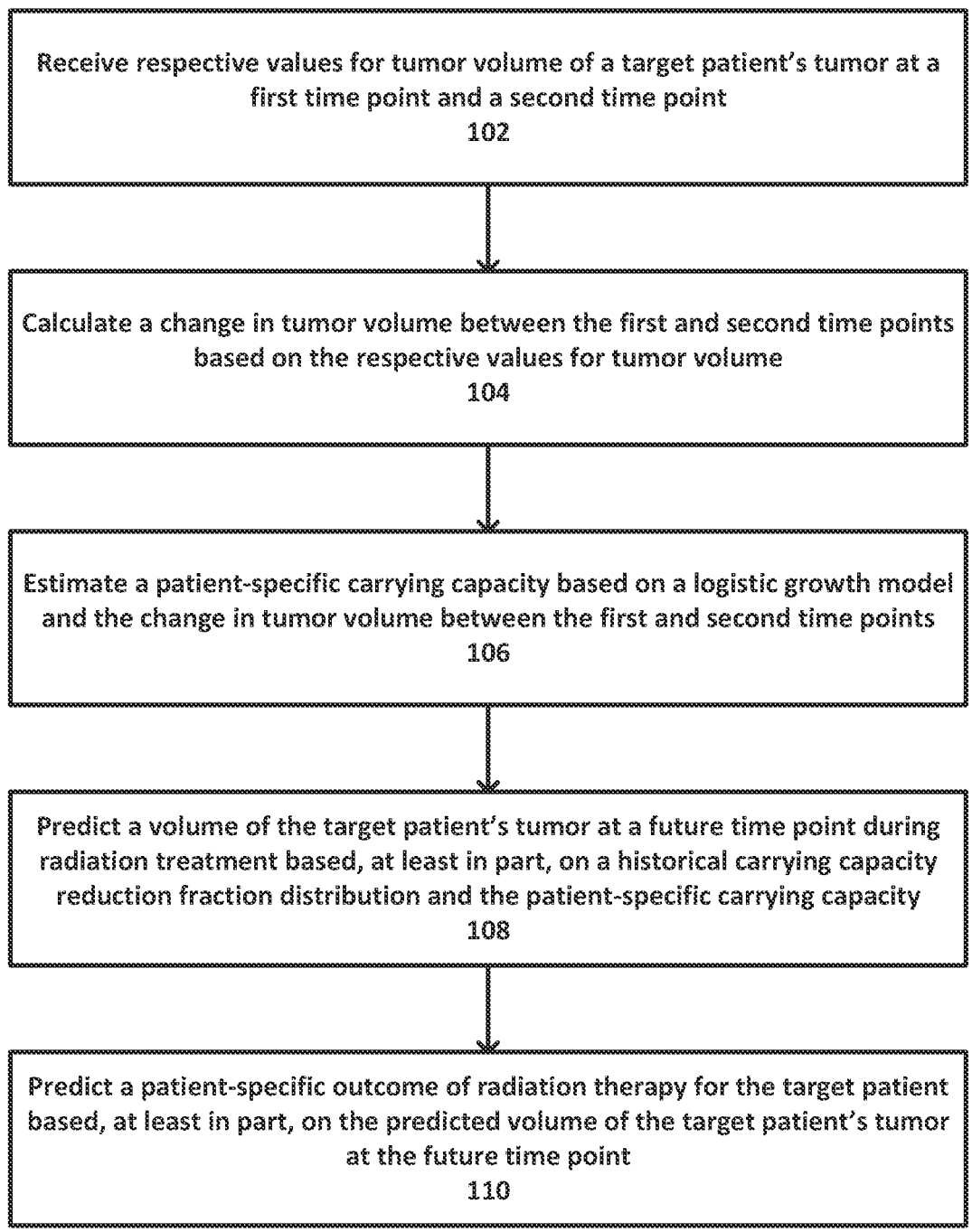
FIG. 1 is a flowchart illustrating example operations for predicting response to and/or outcome of radiation therapy according to implementations described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described with regard to patients having neck and head cancer, it will become evident to those skilled in the art that the implementations are not limited thereto, but are applicable for patients having other types of cancer.

A clinical decision support tool that predicts response to radiotherapy (RT) for individual patients is described herein. For radiotherapy to enter the realm of personalized medicine, it is necessary to model and predict individual patient responses to radiotherapy. As described below, to predict response to radiotherapy for individual patients, a method (sometimes referred to as a "forecasting framework") that combines (1) the learned tumor growth rate ($\lambda$) and (2) carrying capacity reduction fraction ($\delta$) distribution with (3) measurements of volume reduction for a given patient to estimate 6, which is then used to predict patient-specific outcomes for different treatment doses, is described. The model described herein was developed using tumor dynamics as logistic growth and the effect of radiation as a reduction in the tumor carrying capacity, based on the impact of radiation on the tumor microenvironment. The model was then trained, tested, and validated using two different cohorts of cancer patients as described in detail below. Overall, the model is an adaptive Bayesian approach to describe a variety of tumor volume dynamics and combines historically observed patient responses with a few patient-specific tumor volume measurements to accurately predict patient outcomes to inform treatment adaptation and personalization.

The methods described herein can be used to predict response to and/or outcome of radiotherapy, treat, and/or develop a treatment plan for a solid tumor in a subject (or patient). A solid tumor is an abnormal mass of hyperproliferative or neoplastic cells from a tissue other than blood, bone marrow, or the lymphatic system, which may be benign or cancerous. In general, the tumors described herein are cancerous. As used herein, the terms "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of solid cancerous growths, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. Examples of solid tumors are sarcomas, carcinomas, and lymphomas. Leukemias (cancers of the blood) generally do not form solid tumors.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some implementations, the disease is lung carcinoma, rectal carcinoma, colon carcinoma, esophageal carcinoma, prostate carcinoma, head and neck carcinoma, or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In the examples described herein, the tumors originate from head/neck tissues (e.g., originating from the upper aerodigestive tract, including the lip, oral cavity, nasal cavity, paranasal sinuses, pharynx, and larynx, e.g., squamous cell carcinomas originating from the mucosal lining (epithelium)). Although head/neck cancer is used in the examples described herein, this disclosure contemplates that the methods to predict outcome of radiotherapy, treat, and/or develop a treatment plan can be applied to other tumors including, but not limited to, those that originate from lung, colon, rectal, esophageal, prostate. It should be understood that some tumors are metastatic, and originate from an epithelial tissue (and are thus epithelial in origin) but spread to another tissue, e.g., epithelial-origin prostate cancer that has spread to the bones of the pelvis, spine and/or ribs, or lung carcinoma that has metastasized to the adrenal glands, liver, brain, or bones.

An example method for predicting response to and/or outcome of radiation therapy is described below. Personalized RT total dose and dose fractionation prescription has yet to be realized in clinical setting. As noted above, biomarkers such as genomic data have affected decision making for other cancer treatments such as chemotherapy, but the same has not impacted RT. The method described herein addresses the problem of providing personalized RT. The method described herein also provides the patient-specific prediction at an early stage in radiation treatment, which affords the clinician with flexibility to alter and/or supplement RT. Additionally, as described below, the method described herein is able to simulate individual differences in both the varied tumor response dynamics during RT and variable pre-treatment growth dynamics, which include, but are not limited to, no change in tumor volume before RT, transient increases in volume after the start of RT, and various rates of volume reduction during RT. Such simulations have not been achieved by existing methods with proven predictive accuracy.

The example method described herein is applicable to head and neck cancer. Typically, RT for head and neck cancer is a six to seven week treatment with radiation being delivered to the patient on a daily basis. For example, the patient may receive radiation treatments daily Monday through Friday. It should be understood that the patient need not receive radiation treatment every day, and that some protocols deliver radiation more than once per day (e.g., twice a day). Referring now to FIG. 1, an example method for predicting response to and/or outcome of radiation therapy is shown. At step 102, the example method includes receiving (e.g., using computing device 200 of FIG. 2) respective values for tumor volume of a target patient's tumor (e.g., head and neck cancer) for at least two time points. In some implementations, respective values for tumor volume are received for at least two time points prior to radiation and additional time points during therapy. Tumor volume can be derived by analyzing radiological images such as computed-tomography (CT) images. The image analysis can be performed using known image analysis techniques including, but not limited to, segmentation algorithms. Although CT imaging is provided as an example, this disclosure contemplates using other imaging modalities such as magnetic resonance imaging (MRI). In some implementations, radiation treatment is administered using image guidance such as CT. Tumor volume can be derived (e.g., using computing device 200 of FIG. 2) from the radiological images using techniques known in the art.

As described herein, the at least two time points can include a first time point, a second time point, and third time point. For example, the first point in time can be prior to beginning radiation treatment (e.g., at the time of diagnosis or at treatment planning stage). This disclosure contemplates that a radiological image(s) is captured at either or both of these stages. Additionally, the second point in time can be at a beginning of radiation treatment (i.e., just prior to delivery of the first radiation dose). This disclosure contemplates that a radiological image(s) is captured during delivery of radiation therapy (e.g., image guided RT). Further, the third point in time can be during radiation therapy (e.g., first week, second week, third week, fourth week, fifth week, etc. of radiation treatment). As described above, a radiological image is acquired at each point in time, and tumor volume is derived from each radiological image. It should be understood that patient data (e.g., tumor volume) can be collected at more than three time points. At step 104, the method also includes calculating (e.g., using computing device 200 of FIG. 2) a change in tumor volume between the at least two time points $$\left(\frac{\Delta V}{\Delta t}\right)$$

based on the respective values for tumor volume. This is also shown by reference number 402 in FIG. 4.

Referring again to FIG. 1, at step 106, the method also includes estimating (e.g., using computing device 200 of FIG. 2) a patient-specific carrying capacity (K) based on a logistic growth model and the change in tumor volume between the first and second time points. This is also shown by reference number 404 in FIG. 4. As discussed above, the first time point is prior radiation treatment (e.g., diagnosis or treatment planning stage) and the second time point is at the start of radiation therapy (e.g., week 0). The logistic growth model is shown by Equation (1) below.

$$\frac{dV}{dt} = \lambda V \left(1 - \frac{V}{K}\right). \quad (1)$$

where V is tumor volume, $\lambda$ is the intrinsic tumor growth rate [day-1], and K is the tumor carrying capacity. In some implementations, the intrinsic growth rate ($\lambda$) is patient specific. In other implementations, the intrinsic growth rate ($\lambda_{optim}$) is learned from a training data set and applied to all patients.

Referring again to FIG. 1, at step 108, the method also includes predicting (e.g., using computing device 200 of FIG. 2) a volume of the target patient's tumor at a future time point during radiation treatment based, at least in part, on a historical carrying capacity reduction fraction distribution (historical $\delta$-distribution) for a plurality of historical patients and the change in tumor volume between the first and second time points. This is done by calculating an initial patient-specific carrying capacity (see Eqn. (2) below) and then step-wise calculating the reduced carrying capacity at each time point that a radiation dose is to be delivered (see Eqn. (3) below). Thereafter the tumor volume over time can be calculated, as constrained by this serially reduced carrying capacity. This is also shown by reference number 406 in FIG. 4.

Referring again to FIG. 1, at step 110, the method further includes predicting (e.g., using computing device 200 of FIG. 2) a patient-specific outcome of radiation therapy for the target patient based, at least in part, on the predicted volume of the target patient's tumor at the future time point. This is done by simulating the expected tumor volumes for a patient, given the updated patient-specific $\delta$-distribution (see Eqn. (4)), a plurality of times and calculating whether or not the simulated tumor volumes are above or below the volume reduction the respective thresholds association with locoregional control (LRC) or disease-free survival (DFS). Example thresholds for LRC and DFS are provided below. As described herein, respective thresholds for different outcomes can be calculated for a given training data set. The predicted patient-specific outcome can include, but is not limited to, locoregional control (LRC), disease-free survival (DFS), and/or a percentage chance of success of radiation therapy. This is also shown by reference number 408 in FIG. 4.

In some implementations, the method optionally further includes receiving (e.g., using computing device 200 of FIG. 2) a respective value for tumor volume of the target patient's tumor at a third time point. The third time point is during radiation treatment, e.g., at a second, third, fourth, or fifth week of radiation treatment. This disclosure contemplates that a radiological image(s) is captured during delivery of radiation therapy (e.g., patient positioning, or image guided RT). Alternatively or additionally, the future time point is at a sixth week of radiation treatment. It should be understood that the sixth week is the future time point for head and neck cancer. This disclosure contemplates that the future time point may be different for other types of cancer. The method then includes calculating (e.g., using computing device 200 of FIG. 2) a change in tumor volume between the second and third time points based on the respective values for tumor volume, estimating (e.g., using computing device 200 of FIG. 2) a patient-specific carrying capacity reduction fraction ($\delta$) based on the logistic growth model and the change in tumor volume between the second and third time points, and predicting (e.g., using computing device 200 of FIG. 2) the volume of the target patient's tumor at the future time point during radiation treatment based, at least in part, on the patient-specific carrying capacity reduction fraction and the change in tumor volume between the second and third time points. As described above, the predicted volume of the target patient's tumor at the future time point is used to predict a patient-specific outcome of radiation therapy for the target patient. As described below, the tumor volume at the third time point is used to obtain a more accurate prediction as compared to the initial prediction which is based only on historical data.

Additionally, the patient-specific outcome can be predicted for the future time point (e.g., sixth week of radiation treatment) at the start of radiation therapy (week 0), the first week of radiation therapy (week 1), the second week of radiation therapy (week 2), the third week of radiation therapy (week 3), the fourth week of radiation therapy (week 4), and/or the fifth week of radiation therapy (week 5). It should be understood that the patient's clinical information (e.g., tumor volume) at an earlier point in radiation treatment is used to simulate tumor volume dynamics in the future. This disclosure contemplates providing the prediction for the same target patient multiple times (e.g., at weeks 0, 1, 2, 3, 4, 5). The prediction is more accurate as more patient-specific data is collected, e.g., the prediction is more accurate at the fourth week of radiation treatment than at the second week of radiation treatment.

Figure 17:
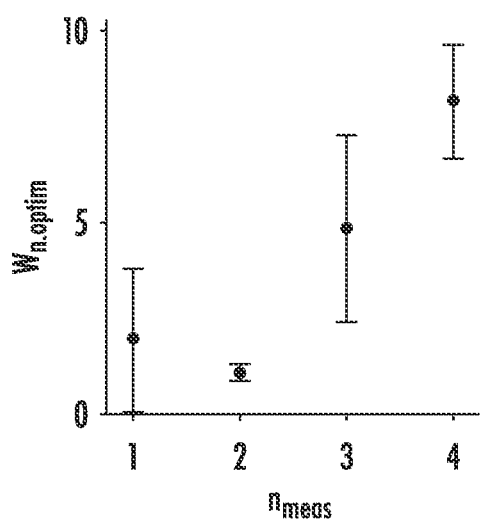

The step of predicting a volume of the target patient's tumor at a future time point in radiation treatment optionally includes maintaining the historical carrying capacity reduction fraction distribution for a plurality of historical patients with comparable disease, and updating the carrying capacity reduction fraction distribution to include the patient-specific carrying capacity reduction fraction for the target patient. The method then includes randomly sampling from the updated carrying capacity reduction fraction distribution, and simulating tumor volume dynamics during radiation treatment for the target patient. Optionally, the method further includes weighting the carrying capacity reduction fraction for the target patient. For example, as radiation therapy progress, the carrying capacity reduction fraction for the target patient (i.e., actual clinical data for the target patient) is increasingly heavily weighted (with weights learned in the training cohort) in the prediction model as compared to the historical δ-distribution. In other words, as the number of patient-specific measurements increases, the relative weight assigned to the carrying capacity reduction fraction for the target patient relative to the training δ-distribution for the n-th clinical measurement increases as learned from historic training data. This is also shown by reference number 410 in FIG. 4. The values for these weights were derived in order to optimize the prediction of LRC in a training set with the inclusion of a given number of weekly volume measurements. The distributions of these optimized weights are shown in FIG. 17.

The patient-specific outcome is predicted by comparing a change in tumor volume at the future time point to a threshold. As described below, the threshold is calculated independently for a training data set. Additionally, it should be understood that it is possible to calculate a respective threshold for different outcomes, e.g., a respective threshold for LRC, a respective threshold for DFS, etc. For example, the change in tumor volume is the difference between tumor volume at the future time point (e.g., week 6) and tumor volume at the start of radiation treatment (week 0). In the examples described herein, this change in tumor volume is predictive of outcome. For example, at week 6, a ΔV greater than or equal to 28.7% had 100% LRC for neck and head cancer, given the patients in the training cohort. This value can adaptively change with additional patients being treated and used for model learning for the next patients. Alternatively or additionally, at week 6, a ΔV greater than or equal to 52.6% had 100% DFS, again based on the patients in the training cohort. This value can adaptively change with additional patients being treated and used for model learning for the next patients. Alternatively or additionally, the change in volume at the future time point can be used to predict a percentage chance of success of radiation therapy. It should be understood that the thresholds for LRC and DFS are provided as examples from the analyzed patient cohort. This disclosure contemplates that a threshold may have a different value depending on the type of tumor, and with additional patient data being included in model training.

Optionally, the method further includes treating the target patient based on the predicted patient-specific outcome. In other words, the predicted patient-specific outcome can be used to inform treatment decisions and/or planning. In some implementations, RT is escalated or de-escalated based on the predicted patient-specific outcome. For example, if the target patient is not predicted to have a favorable outcome (e.g., LRC or DFS), the clinician may prescribe additional and/or alternative treatments for the target patient. Alternatively or additionally, the clinician may adjust the parameters of the radiation treatment (e.g., total dose, dose per fraction). On the other hand, if the target patient is predicted to have a favorable outcome (e.g., LRC or DFS), the clinician may adjust the parameters of the radiation treatment, which may include reducing radiation dose to limit exposure. As described above, the methods are used to make outcome predictions in the early stages of radiation treatment (e.g., week 2, week, 3, week 4, week 5). This provides the clinician with flexibility to make adjustments to the total dose and/or dose per treatment.

It should be appreciated that the logical operations described herein with respect to the various figures may be implemented (1) as a sequence of computer implemented acts or program modules (i.e., software) running on a computing device (e.g., the computing device described in FIG. 2), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 2:
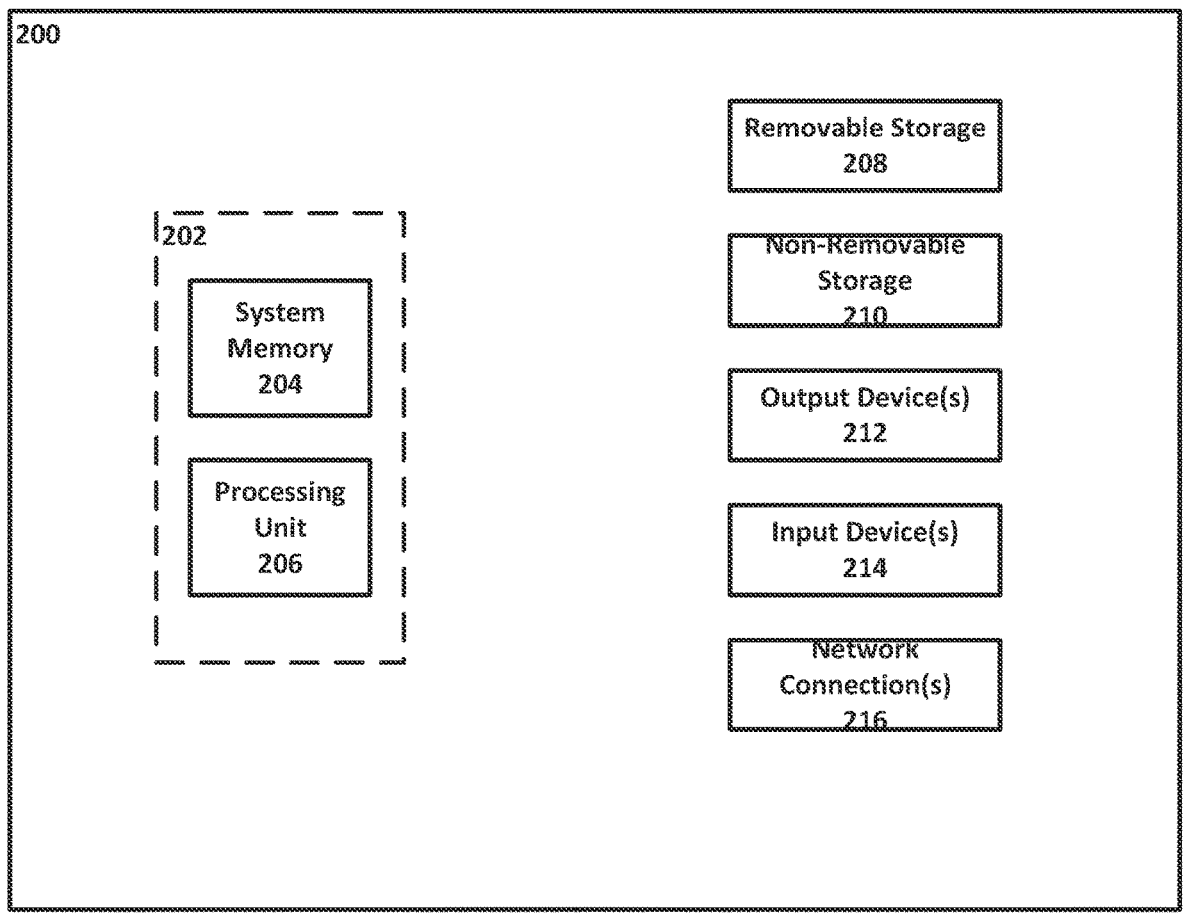
FIG. 2 is an example computing device.

Referring to FIG. 2, an example computing device 200 upon which the methods described herein may be implemented is illustrated. It should be understood that the example computing device 200 is only one example of a suitable computing environment upon which the methods described herein may be implemented. Optionally, the computing device 200 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 200 typically includes at least one processing unit 206 and system memory 204. Depending on the exact configuration and type of computing device, system memory 204 may be volatile (such as random access memory (RAM)), non-volatile (such as read-only memory (ROM), flash memory, etc.), or some combination of the two. This most basic configuration is illustrated in FIG. 2 by dashed line 202. The processing unit 206 may be a standard programmable processor that performs arithmetic and logic operations necessary for operation of the computing device 200. The computing device 200 may also include a bus or other communication mechanism for communicating information among various components of the computing device 200.

Computing device 200 may have additional features/functionality. For example, computing device 200 may include additional storage such as removable storage 208 and non-removable storage 210 including, but not limited to, magnetic or optical disks or tapes. Computing device 200 may also contain network connection(s) 216 that allow the device to communicate with other devices. Computing device 200 may also have input device(s) 214 such as a keyboard, mouse, touch screen, etc. Output device(s) 212 such as a display, speakers, printer, etc. may also be included. The additional devices may be connected to the bus in order to facilitate communication of data among the components of the computing device 200. All these devices are well known in the art and need not be discussed at length here.

The processing unit 206 may be configured to execute program code encoded in tangible, computer-readable media. Tangible, computer-readable media refers to any media that is capable of providing data that causes the computing device 200 (i.e., a machine) to operate in a particular fashion. Various computer-readable media may be utilized to provide instructions to the processing unit 206 for execution. Example tangible, computer-readable media may include, but is not limited to, volatile media, non-volatile media, removable media and non-removable media implemented in any method or technology for storage of information such as computer readable instructions, data structures, program modules or other data. System memory 204, removable storage 208, and non-removable storage 210 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 206 may execute program code stored in the system memory 204. For example, the bus may carry data to the system memory 204, from which the processing unit 206 receives and executes instructions. The data received by the system memory 204 may optionally be stored on the removable storage 208 or the non-removable storage 210 before or after execution by the processing unit 206.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

In the example below, tumor dynamics are modeled as logistic growth and the effect of radiation is modeled as a reduction in the tumor carrying capacity, motivated by the impact of radiation on the tumor microenvironment. The model was assessed on weekly tumor volume data collected for two independent cohorts of head and neck cancer patients from Moffitt Cancer Center (MCC) and MD Anderson Cancer Center (MDACC) that received 66-70 Gy in standard daily fractions or with accelerated fractionation. To predict response to radiotherapy for individual patients, a forecasting framework that combines the learned tumor growth rate and carrying capacity reduction fraction ($\delta$) distribution with measurements of volume reduction for a given test patient to estimate $\delta$, which is used to predict patient-specific outcomes, is described.

The model fit data from MCC with high accuracy with patient-specific $\delta$ and a fixed tumor growth rate across all patients. The model fit data from an independent cross-validation cohort from MDACC with comparable accuracy using the tumor growth rate learned from the MCC cohort, demonstrating transferability of the growth rate. The forecasting framework predicted patient-specific outcomes with >89% sensitivity and >96% specificity for locoregional control and with >83% sensitivity and >89% specificity for disease-free survival after two weeks of radiotherapy, with increasing accuracy with additional data points.

These results show that the forecasting framework can describe a variety of tumor volume dynamics. Combining historically observed patient responses with a few patient-specific tumor volume measurements allows for the accurate prediction of patient outcomes, which may inform treatment adaptation and personalization.

Materials and Methods

Mathematical Model of Carrying Capacity Reduction

The change in tumor volume, V [cc], over time is modeled by logistic growth[15]:

$$\frac{dV}{dt} = \lambda V \left(1 - \frac{V}{K}\right),$$

which is Eqn. (1) above. In the above equation, $\lambda$ is the intrinsic volumetric growth rate [day$^{-1}$] and K is the tumor carrying capacity [cc]. The intrinsic volumetric growth rate translates into volume doubling time as $\ln(2)/\lambda$. Without therapy, the tumor volume increases in logistic fashion, approaching its carrying capacity.

$$PSI \equiv \frac{V_0}{K_0},$$

where $V_0$ is the tumor volume prior to the first dose of RT, usually obtained from patient positioning cone-beam CT images. This can also be obtained by other radiology imaging such as diagnostic CT, PET CT, or MRI on an MRLinac radiation device. The carrying capacity of the tumor prior to the first dose of RT, $K_0$, is calculated as:

$$K_0 = \frac{V_0 V_{plan}(e^{\lambda \Delta t} - 1)}{V_{plan} e^{\lambda \Delta t} - V_0}, \quad (2)$$

where $V_{plan}$ is the volume abstracted at the time of initial RT planning (typically a few weeks before the start of RT), and $\Delta t$ is the time interval between the measurements of $V_{plan}$ and $V_0$. During radiation, the complex microenvironment in the radiation target volume is altered (FIG. 3A). Thusly, the effects of RT are modeled by an instantaneous reduction in carrying capacity given by:

$$K_{pos\text{-}RT\text{-}Fx} = K_{pre\text{-}RT\text{-}Fx}(1-\delta), \quad (3)$$

where $K_{post\text{-}RT\text{-}Fx}$ is the tumor carrying capacity after a radiation fraction and $\delta$ is the fraction by which the carrying capacity is reduced with each radiation fraction. $\delta$ is defined between 0 and 1, where when $\delta=0$ there is no reduction of carrying capacity and when $\delta=1$ there is 100% reduction in carrying capacity. Both $\lambda$ and $\delta$ are assumed to remain constant throughout treatment.

The 3-parameter model proposed here can simulate a variety of tumor growth dynamics in response to RT. When RT is applied and the carrying capacity after RT remains greater than the tumor volume ($K_{post\text{-}RT\text{-}Fx} > V_{pre\text{-}RT\text{-}Fx}$), tumor growth is slowed (FIG. 3B, Case 1). Conversely, when the carrying capacity after RT is less than the volume at the time of RT ($K_{post\text{-}RT\text{-}Fx} < V_{pre\text{-}RT\text{-}Fx}$), tumor volume declines and approaches $K_{post\text{-}RT\text{-}Fx}$ from above (FIG. 3C, Case 2). In this case, A now assumes the rate at which the tumor declines; a visualization of the intrinsic response rate.

Patient Data

The model was trained against a cohort of 17 head and neck cancer patients treated at Moffitt Cancer Center (MCC) with a total of 66-70 Gy RT in 2 Gy weekday fractions. The independent cross-validation cohort from the MD Anderson Cancer Center (MDACC) comprised 22 head and neck cancer patients treated with a total of 66-70 Gy RT (2 or 2.12 Gy weekday fractions or with accelerated fractionation). Tumor volume measurements were derived from computed tomography (CT) scans at time of RT planning, just before the first RT dose, and weekly scans during the course of treatment. Patient demographics and clinical parameters are described in Table 1 (FIG. 9). Statistical comparison of the two cohorts showed no significant differences in tumor, lymph node and metastases (TNM) stages. While the primary site of the MCC cohort was predominantly oropharyngeal cancer, the majority of primary sites of MDACC patients included tonsil and base of tongue. Locoregional control (LRC), disease-free survival (DFS), and overall survival (OS) data were collected for both cohorts.

Parameter Optimization

The model was initially fit to patient data by finding a pair of $\lambda$ and $\delta$ values that minimized root mean square error (RMSE) of the model for each patient. After systematic parameter reduction analysis (supplementary methods, Table 2 (FIG. 10)), it was found that $\lambda$ could be set uniform ($\lambda_{optim}$) across the entire cohort, without losing any information. Optimization and parameter reduction details are described below in the supplementary materials and methods discussion below. The value for $\lambda_{optim}$ was selected by performing a full grid search of $\lambda \in (0.055 \text{ day}^{-1}, 0.69 \text{ day}^{-1})$ with a step size of 0.025, in order to find the value of A that minimized fitting error for the entire training cohort. The upper bound for A was set as one cell division or volume doubling per day (ln 2), and the lower bound was calculated by a 92% cell loss factor with one cell division per day.[30]

Statistical Methods

Patient characteristic prevalence levels were compared between the two cohorts using Fisher's Exact Test to test the null hypothesis that there are no non-random associations between the presence and absence of the characteristic in the two cohorts, and the p-values for each characteristic are reported in Table 1. For the remainder of the study, distributions of fitted parameters were compared using a Mann-Whitney U-test to test the null hypothesis of distributions with equal medians. A p-value $p<0.05$ indicated significantly different distributions.

Leave-One-Out Prediction Study

Due to the low failure rate in the treatment of head and neck cancers with RT, only six local failures and seven distant failures were observed across both cohorts. In order to deal with this low number of events, all work in forecasting patient outcomes was done as a series of 39 leave-one-out cross-validation studies, where the forecasting model was trained on 38 patients to make predictions for the 39th patient.[31] This type of analysis is classified as a type 1b analysis in the TRIPOD statement recommendations for predictive models, which is considered appropriate for model development and internal validation in the context of limited data.[32] For a given N-1 training cohort of patients, tumor volume reduction cutoffs at a given week of RT that separates the cohort were identified such that one of groups has zero LRC or DFS failures. Cutoff values that maximize the significance of curve separation of the LRC and DFS Kaplan-Meier survival curves were selected, measured by log-rank p-values.

Forecasting Pipeline

Figure 4:
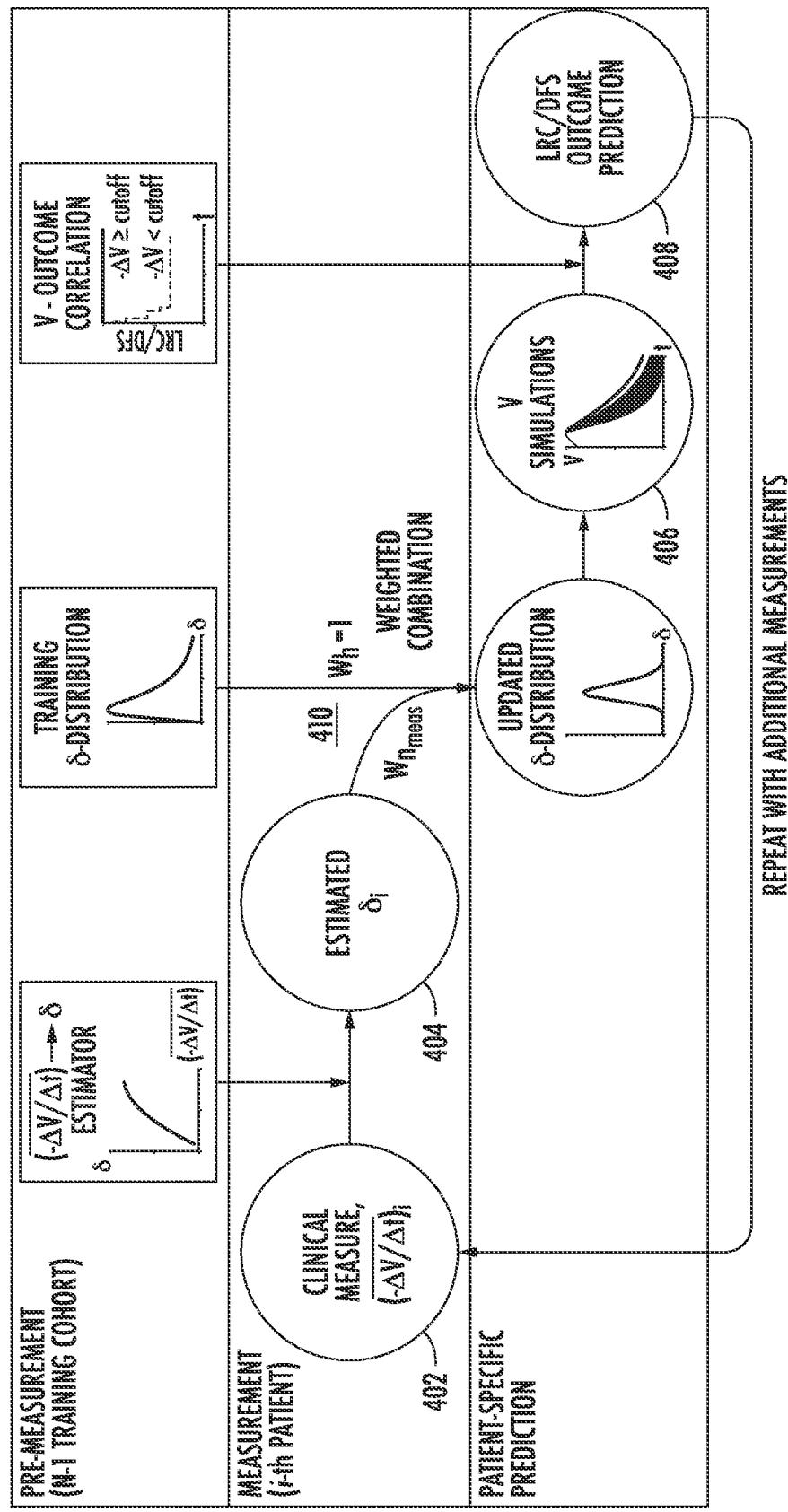
FIG. 4 is a flowchart representation of forecasting pipeline that adaptively combines training data and new patient measurements. The pipeline is divided into three phases: pre-measurement based on the training cohort, measurements for the i-th patient, and patient-specific predictions. The squares represent information learned from the training cohort; circles represent information measured or calculated for an individual patient. The entire prediction pipeline can be repeated with the additional measurements from the patient.

As the model simulates tumor volume dynamics, changes in tumor volume were correlated with LRC and DFS. To predict tumor volume changes and thus outcomes, a forecasting pipeline that adaptively combines the training data with specific clinical measurements of the left-out test patient at appropriate weights was developed (FIG. 4). Weekly tumor volume reduction was evaluated as a function of radiation-induced carrying capacity reduction fraction, $\delta$. For a given test patient, i, the average weekly volume reduction since the start of RT, $$\left(-\overline{\frac{\Delta V}{\Delta t}}\right)_i,$$

is used to estimate a value of $\delta$ for that patient ($\delta_i$). This estimate is used to update the training-derived $\delta$-distribution:

$$\text{Lognormal} \sim \left( \mu_i = \frac{\mu_h + \ln(\delta_i) \cdot w_n \cdot n_{meas}}{w \cdot n_{meas} + 1}, \sigma_i = \frac{\sigma_h}{n_{meas} + 1} \right) \quad (4)$$

where $\mu_i$ and $\sigma_i$ are the updated parameters for the patient-specific $\delta$-distribution, $\mu_h$ and $\sigma_h$ are the parameters for the training $\delta$-distribution, $w_{n_{meas}} \in (0,10)$ is the weight given to the patient's clinical measures relative to a weight of $w_h=1$ given to the training $\delta$-distribution for the n-th clinical measurement, and $n_{meas}$ is the number of measurements being considered. This formulation allows the distribution to shift towards $\delta_i$ and to narrow as the number of measurements increases.

Individual patient-specific predictions are made by randomly sampling $\delta$ from the updated $\delta$-distribution and simulating tumor volume dynamics given the patient's specified treatment schedule. From pre-radiation volume data without any on-treatment measurements ($n_{meas}=0$), predictions are made by sampling directly from the training $\delta$-distribution. Model predicted tumor volumes by week six of radiation below or above the LRC and DFS thresholds determined for each training cohort are classified as true positive, false positive, true negative or false negative relative to the clinically observed tumor volume. Patients without tumor volume measurements at week 6 were excluded from the prediction analysis (n=3; 8%).

Results

Model Calibration to Training Cohort

Figure 12:
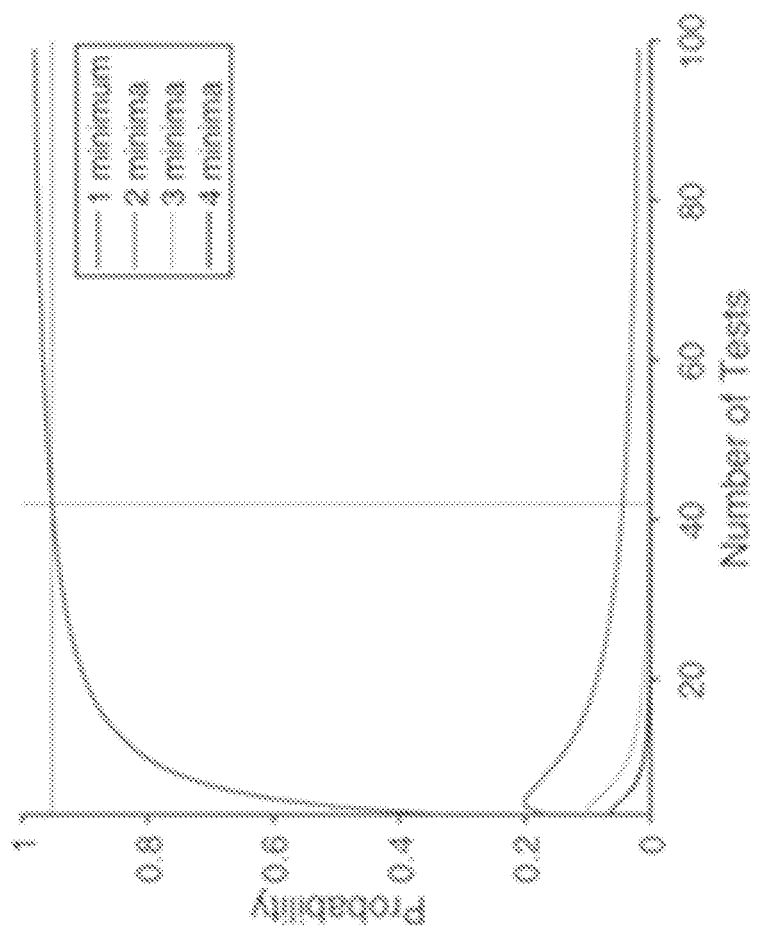
FIG. 12 shows calculating number of simulations to find global optima. Plots of the probability of varying number of global minima as a function of the number of optimizations run, given that only one minimum is observed[5]. Cross-hairs indicate the selected number of runs (42), which yields a probability of approximately 95% that the observed local minimum is a global minimum.

The model training and parameter optimization with three patient-specific parameter values demonstrated that the proposed model can fit a variety of pre- and on-treatment tumor volume dynamics. Across the entire cohort, the model fit individual volume measurements with an average normalized root mean square error of ⟨nRMSE⟩=0.098 (FIGS. 11A and 11B). The distribution of optimized values for individual growth rate, $\lambda$, spanned the entire bounded range, while the optimized values for the carrying capacity reduction fraction for each RT dose fraction, $\delta$, were less than 0.1 for each patient (FIG. 11C). Notably, three patients had $\lambda$ values at the upper bound. However, a number of values for the upper bound were tried, and the model always fits $\lambda$ to the upper bound for these patients. Model calibration and parameter optimization was performed 42 times in order to reach 95% probability that the optimizer was finding globally optimal results (FIG. 12). In the case that 2 optima were found, then the more frequently occurring parameters were selected.

Model Simplification by Parameter Reduction

Figure 13:
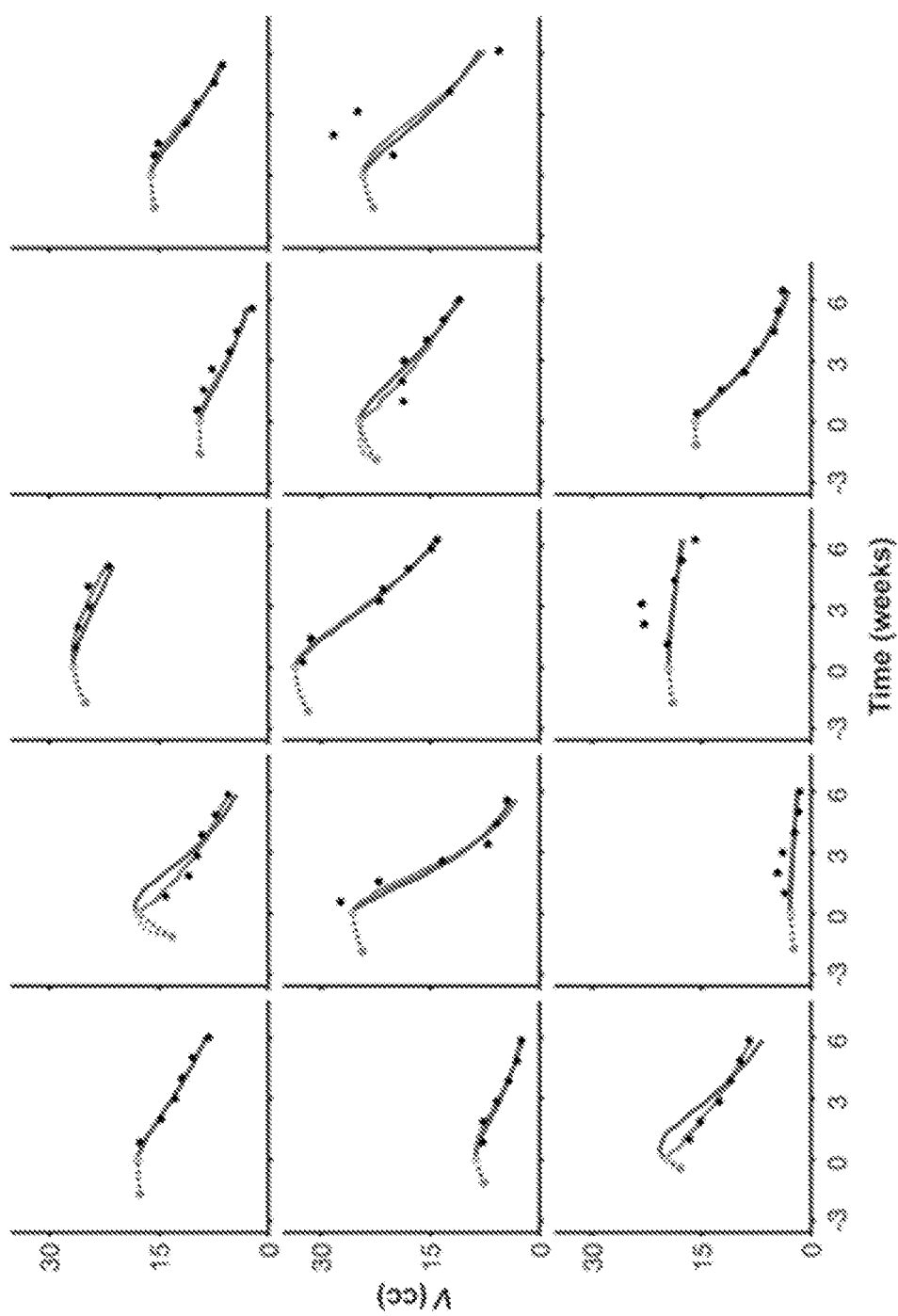
FIG. 13 shows model fit results for the remaining 14 patients from the training cohort with uniform A and patient-specific δ values. Magenta curves (dashed for pre-treatment calculations and solid for on-treatment fits) show volume trajectories from the full model with patient-specific A values; blue curves (dashed for pre-treatment calculations and solid for on-treatment fits) show volume trajectories from the reduced model using $\lambda_{optim}$ across all patients.

Uncertainty associated with each parameter estimate leads to a decrease in the confidence and predictive power of the model; thus parameter reduction may decrease uncertainty and increase confidence and predictive power. Which of the parameters that could be defined as uniform across the entire training cohort with minimal cost to the model goodness-of-fit was explored. Based on Akaike Information Criterion (AIC) and Bayesian Information Criterion (BIC), it was found that $\lambda$ could be set to a fixed value across the entire cohort with minimal reduction to the fitting capacity of the model. It was found that $\lambda_{optim}=0.13$ day$^{-1}$, which corresponds to a tumor volume doubling time of 5 days, to minimize nRMSE across the entire training cohort (FIG. 5B). Setting $\lambda_{optim}=0.13$ day$^{-1}$ uniform across all patients resulted in fits not noticeably different from the results of the original model (⟨nRMSE⟩=0.136 vs. ⟨nRMSE⟩=0.098; FIGS. 5A-5D; FIG. 13). The calculated values of PSI did not vary significantly between the two models (p=0.78; FIG. 5D), despite A varying across a large range of values in the full model (FIGS. 11A-11C). The distributions of the fitted values of $\delta$ also did not vary significantly between the full and reduced models (p=0.86) demonstrating that setting $\lambda$ uniform across the cohort did not alter the estimation of $\delta$ (FIG. 5D).

Model Cross-Variations

Figures 14A, 14B:
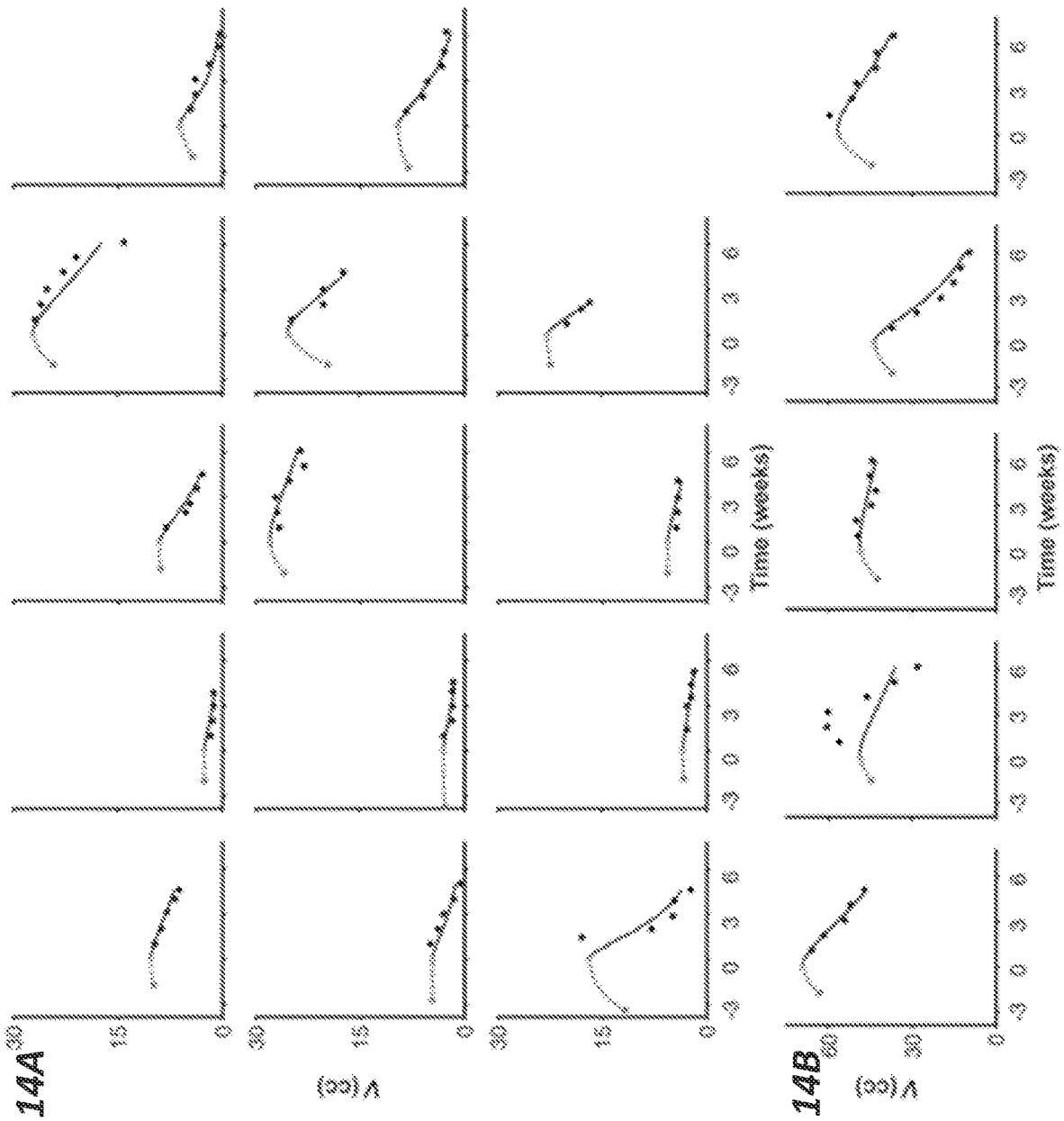
FIGS. 14A and 14B show model fit results for the remaining 19 from the cross-validation cohort with uniform A learned from training cohort and patient-specific δ values.
Figures 15A, 15B:
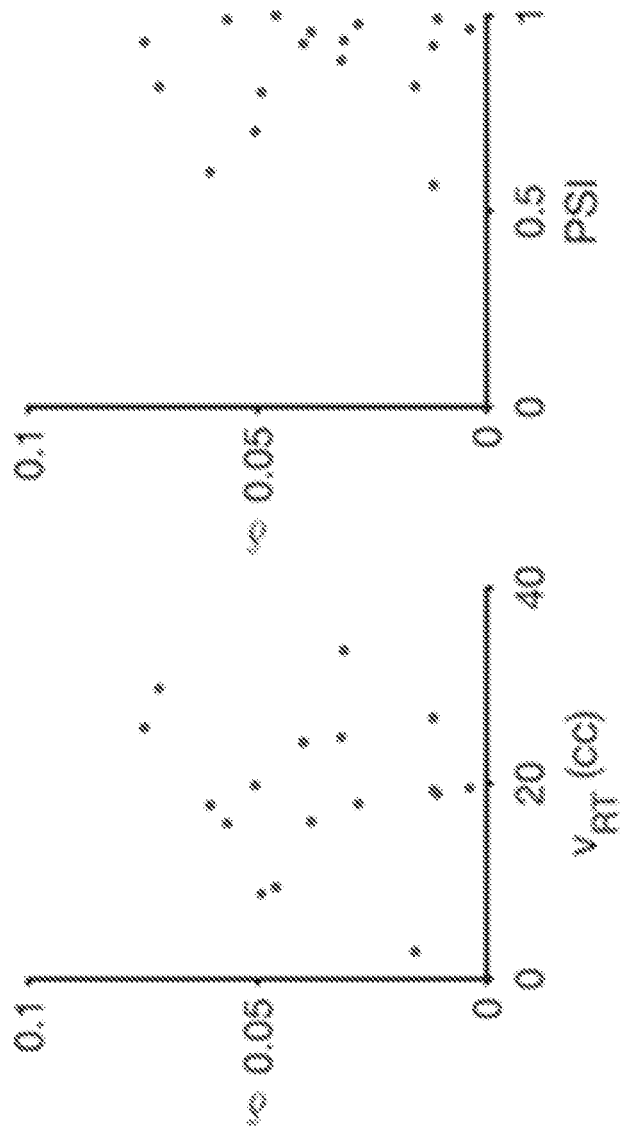
FIGS. 15A and 15B show pre-treatment measurements are insufficient to predict δ.

To cross-validate the reduced model with the learned $\lambda_{optim}$, calculated K based on $\lambda_{optim}$ and pre-RT data points (eqn. (3)), and patient-specific $\delta$, the capacity of the model to fit an independent patient dataset from MDACC (patient characteristics described in Table 1) was tested. The reduced version of the model with $\lambda_{optim}$ learned from the training cohort fits pre- and on-treatment tumor volume dynamics similar to those seen in the training cohort with high accuracy (⟨nRMSE⟩=0.131; FIGS. 6A-6D; FIG. 14). This is despite the fact that some tumor volumes in the cross-validation cohort were up to two times larger than those in the training cohort, even though the distribution of starting volumes are statistically indistinguishable between the two cohorts (p=0.55; FIG. 6C). The distribution of PSI values of the training cohort and the cross-validation cohort are not significantly distinguishable demonstrating similarity in terms of pre-treatment growth between the two cohorts (p=0.77; FIG. 6D). Additionally, the fitted values of $\delta$ did not vary significantly between the two cohorts, indicating that the on-treatment dynamics, as captured by the model, are also similar between the two cohorts (p=0.66; FIG. 6D). Due to the wide range of RT response dynamics and distribution of $\delta$ values, pre-treatment dynamics alone are unable to accurately predict $\delta$ (FIGS. 15A and 15B).

Calibrating Prediction Pipeline

Figure 7A:
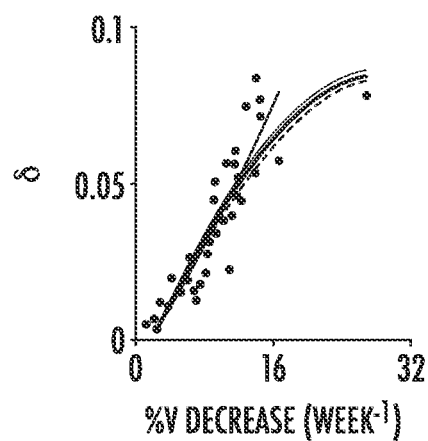
FIGS. 7A-7F show prediction pipeline inputs and results for the 39 leave-one-out studies.

In order to estimate $\delta$ from historic response data in the training cohort and early patient-specific on-treatment data points, an estimator for S was created using average volume reduction per week $$\left(-\frac{\overline{\Delta V}}{\Delta t}\right)$$

as an input. The correlation of $$-\frac{\overline{\Delta V}}{\Delta t}$$

with the fitted S value for each patient in the training cohort can be described as the following quadratic relation (FIG. 7A):

$$\delta = \beta_1 \left(-\frac{\overline{\Delta V}}{\Delta t}\right)^2 + \beta_2 \left(-\frac{\overline{\Delta V}}{\Delta t}\right) + \beta_3. \quad (5)$$

Figure 7B:
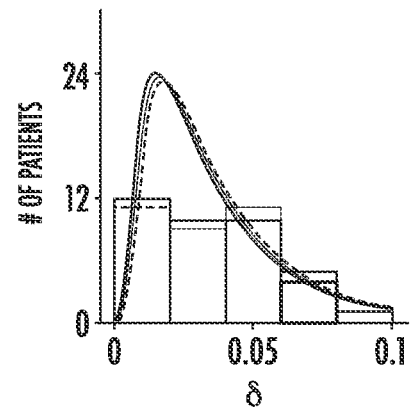
Figure 7C:
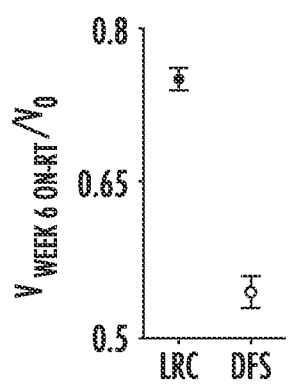
Figure 7D:
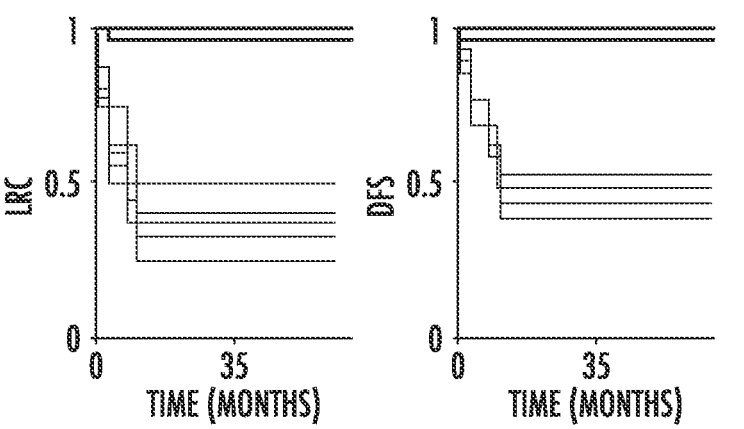
Figure 7E:
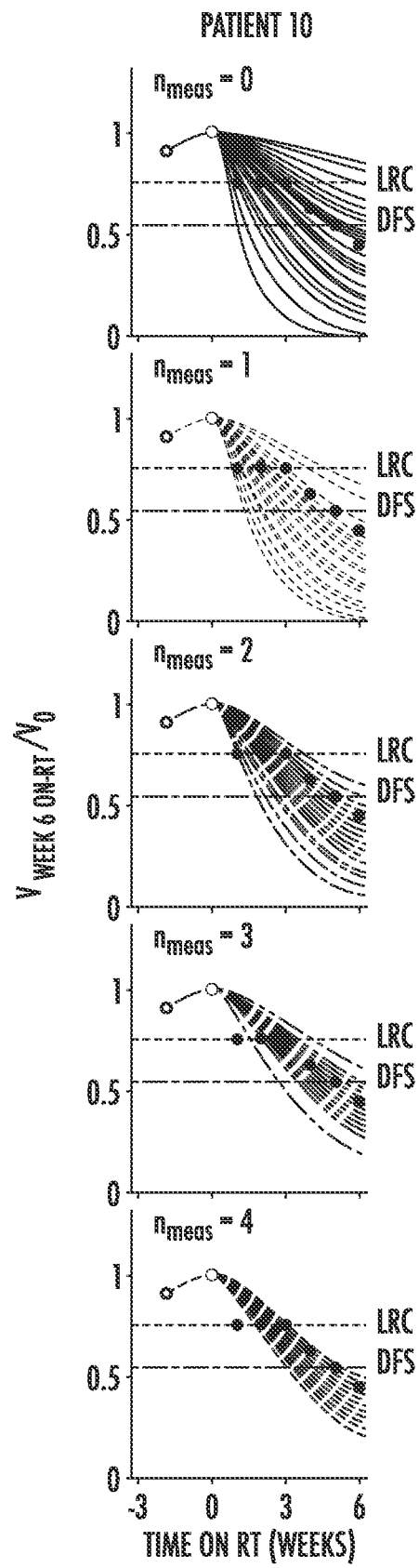
Figure 7F:
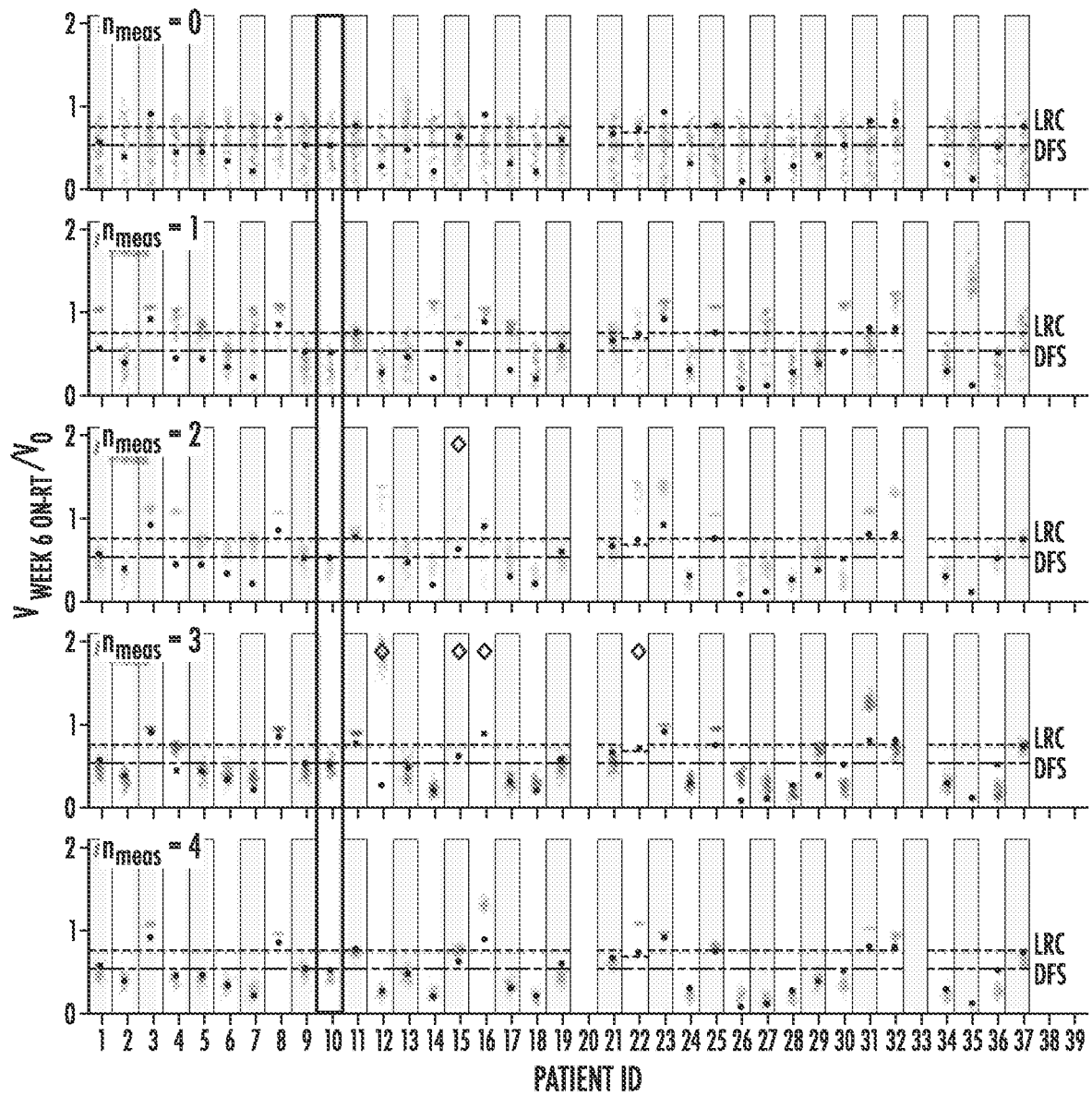
Figure 16A:
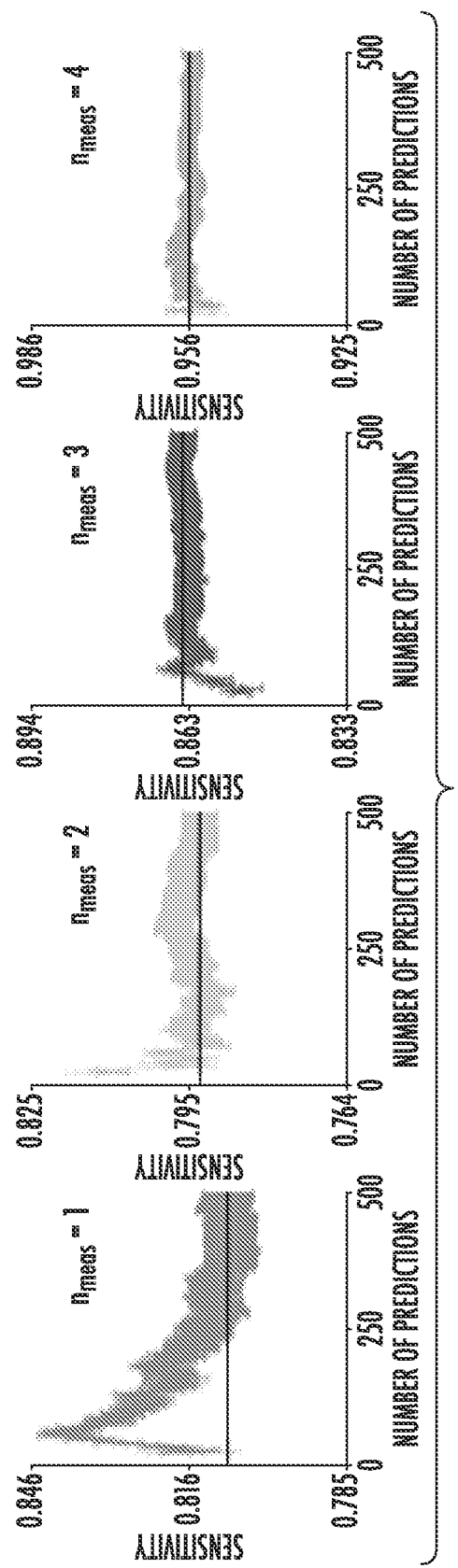
FIGS. 16A and 16B show effect of number of prediction simulations on LRC prediction results for the MCC training cohort.
Figure 16B:
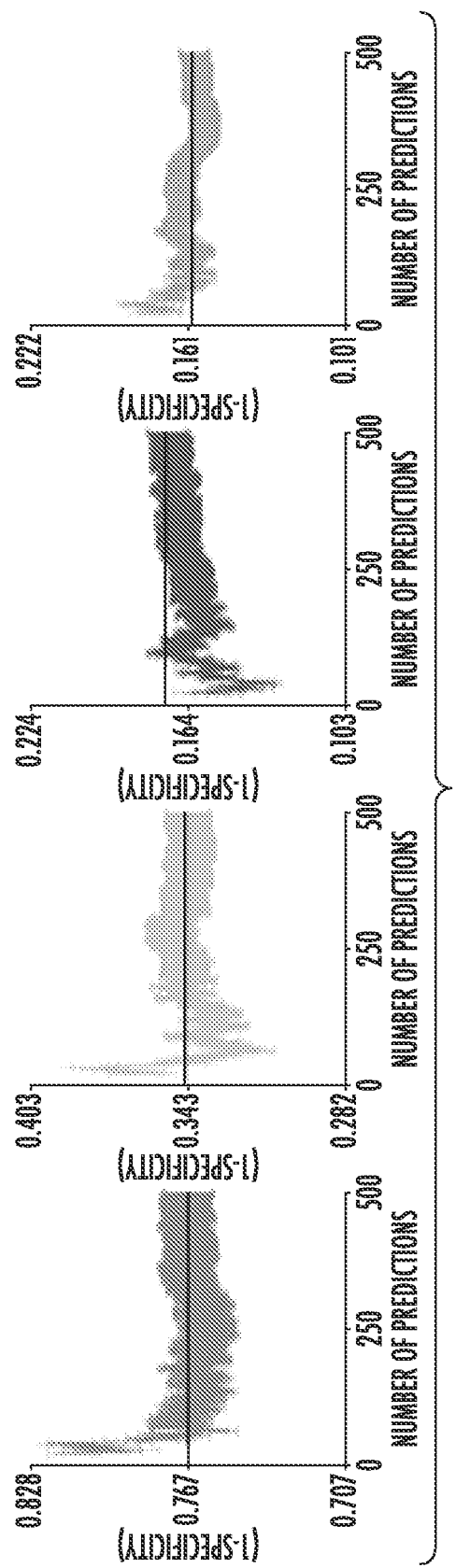

The $\delta$ values for each training cohort in the leave-one-out analysis were fit to a lognormal distribution (FIG. 7B). Numerical values for the $\beta$ coefficients and $\delta$-distribution parameters are described in the supplemental materials and methods discussion below. For the leave-one-out cross-validation of model predictive power analysis, the tumor volume reduction cutoff after 6 weeks of RT that perfectly separates treatment outcomes was derived such that one of groups has zero LRC or DFS failures, for each N−1 training cohort of patients. Cutoff values that maximize the significance of curve separation of the LRC and DFS Kaplan-Meier survival curves were selected (FIGS. 7C and 7D). Treatment response predictions were simulated with different weights $w_{nmeas}$ relative to w=1 for the historical δ-distribution for each number of clinical on treatment measurements, $n_{meas}$. This was done with 500 predictions as the analysis showed this to be sufficient for stable results despite the random sampling from the δ-distribution (FIG. 16). Across all training cohorts in the leave one out analysis, the optimal weights were $w_{nmeas}$<2 for $n_{meas}$≤2, and $w_{nmeas}$>2 on average for all $n_{meas}$≥3 (FIG. 17). 100 prediction simulations for each left-out patient performed using the $\lambda_{optim}$ and $w_{n,optim}$ learned from the corresponding training cohorts are displayed in FIGS. 7E and 7F.

Evaluating Forecasting Pipeline Performance

Figure 8A:
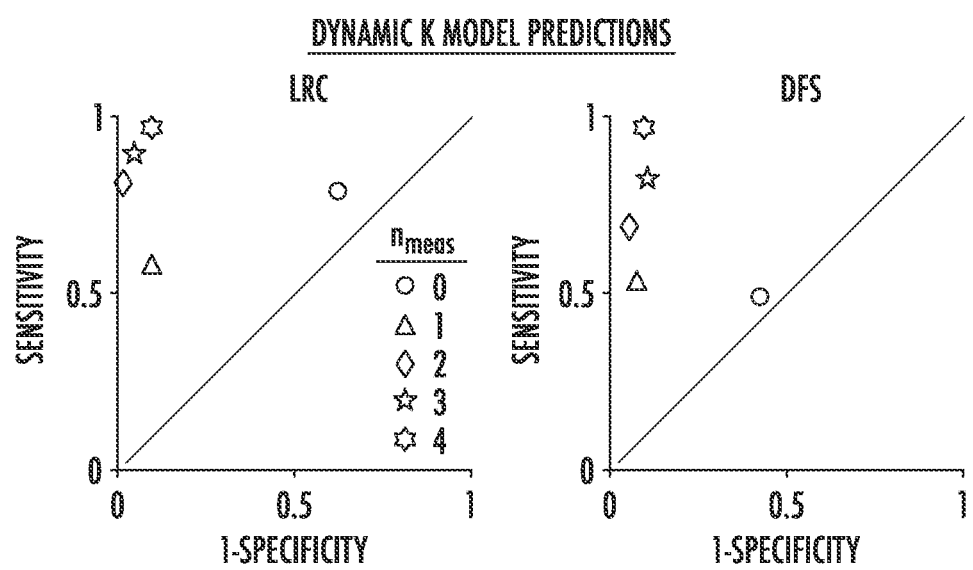
FIGS. 8A-8C show predicting patient outcomes using the dynamic carrying capacity model with the prediction pipeline vs volume reduction alone.
Figure 8B:
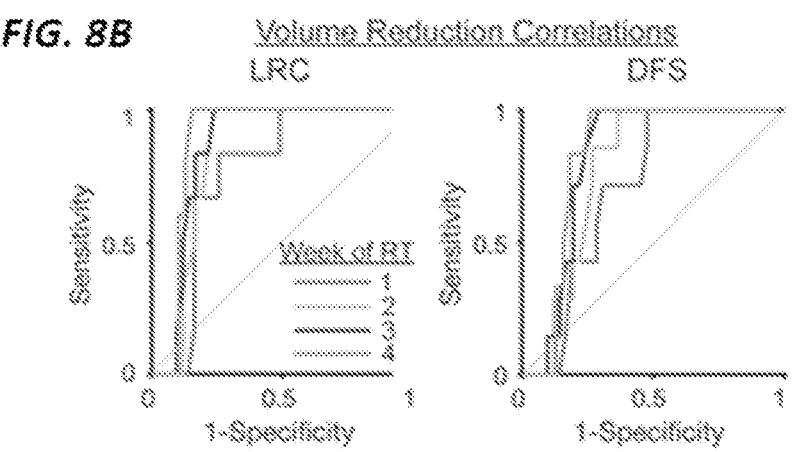
Figure 8C:
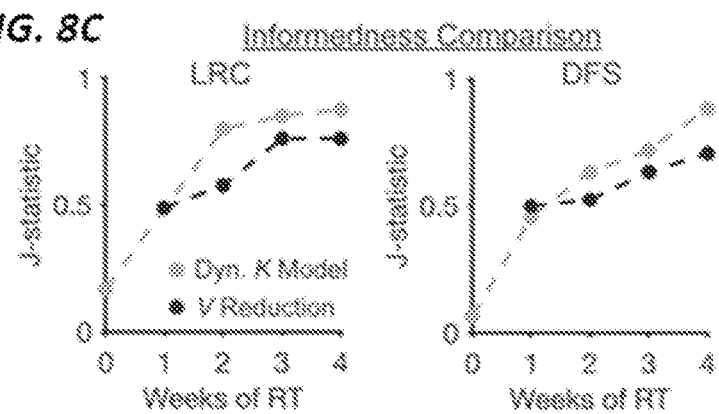
Figure 17A:
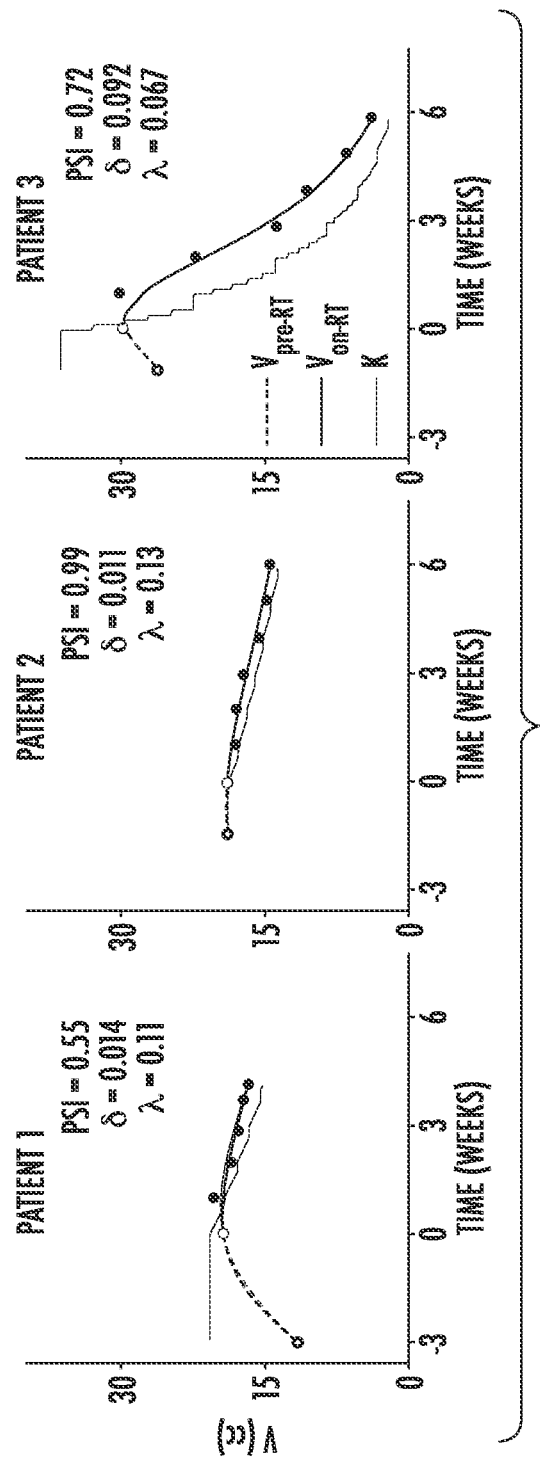
FIG. 17 illustrates plots of the $w_{n,optim}$ for $n_{meas}$=1-4. Error bars indicate standard deviations. All 4 weight distributions are statistically distinct from each other (p<0.05 y Mann-Whitney U-test).

Model predictions yielded sensitivity and specificity slightly above the chance line with $n_{meas}$=0 for both LRC and DFS prediction. Model predictions after inclusion of tumor volume measurements after one week of radiation yielded specificities greater than 0.9 for both outcomes, although with lower sensitivities of less than 0.6 for both LRC and DFS. As early as after two weeks of radiotherapy, the forecasting framework predicted patient-specific outcomes with >89% sensitivity and >96% specificity for LRC, and with >83% sensitivity and >89% specificity for disease-free survival. Additional on-RT measurements, $n_{meas}$=3-4, further increased prediction specificity (FIG. 8A). In order to evaluate the predictive power provided by the model compared to the prognostic capacity of volume reduction measurements alone, ROC curves for absolute volume reduction for weeks 1-4 of RT, relative to the start of RT were calculated (FIG. 8B; supplementary methods). While tumor volume reduction alone has predictive power, the dynamic carrying capacity model outperforms volume reduction alone with the inclusion of at least one measurement of treatment response for both LRC and DFS prediction, as evaluated by Youden's J-statistic[33] (FIG. 8C; supplementary methods).

Discussion

A mathematical model of tumor volume dynamics in response to radiotherapy with a dynamic carrying capacity modeled as an instantaneous function of therapy is described herein. Previously, Hahnfeldt, et. al. presented a model with a dynamic carrying capacity modeled as a continuous function based on the degree of vascularization, in order to model the impact of anti-angiogenic drugs[34]. Several models have modeled a changing tumor microenvironment as a dynamic carrying capacity, by modeling the effects of immune predation, immune-mediated tumor stimulation, nutrient availability in the tumor microenvironment[35-37]. In contrast to these models, the model described herein assumes carrying capacity reduction to be an emergent multifactorial property.

This model, with three patient-specific parameters (i.e., the intrinsic volumetric growth (λ), the tumor carrying capacity (K), the carrying capacity reduction fraction (δ)) in the full version, and two patient-specific parameters in the reduced version (i.e., the tumor carrying capacity (K) and the carrying capacity reduction fraction (δ), where $\lambda_{optim}$ is learned from the training cohort), is able to simulate individual differences in both the varied tumor response dynamics during RT and variable pre-treatment growth dynamics, which include, but are not limited to, no change in tumor volume before RT, transient increases in volume after the start of RT, and various rates of volume reduction during RT. Previous attempts to model the effect of radiation with an LQ-model related survival rate have been unable to capture some of these diverse behaviors[15,17], which motivated the inclusion of additional variables and parameters describing the dynamics of 'doomed' cells dying from radiation[38-40], yielding an ill-posed mathematical problem with currently collected data[41]. The ability to model radiation response dynamics with a single variable and fewer parameters as demonstrated herein opens up the possibility of reliably predicting individual patient responses to therapy, and subsequently the potential to stratify patients for adaptation and thus personalization of radiation therapy.

Both the full version of the model with three patient-specific parameters and the reduced model with two patient-specific parameters fit the data with low error (average nRMSE<0.14) demonstrating that modeling the impact of RT on the tumor microenvironment may be sufficient to model patient-specific tumor volume dynamics. Furthermore, the fitting results from the reduced model with a constant growth rate, λ, across the entire cohort show that inter-patient heterogeneity can be captured in the PSI and carrying capacity reduction fraction, δ, vis-a-vis traditional simulations of patient-specific growth rates[42-44].

Cross-validation of the reduced model with an independent dataset showed promising results that imply that it may be possible to learn a value for a patient-uniform tumor growth rate λ from an external or historical cohort. In this case, all patient heterogeneity would be described by patient-specific PSI and δ values. Notably, even if λ is known a priori, two pre-treatment volume measurements are needed to calculate PSI. Here, it is demonstrated that routinely collected data at radiation simulation and before the first dose delivery may be used to inform PSI.

The presented prediction pipeline, which utilizes the combination of a training parameter distribution and preliminary parameter estimates from available clinical measures, showed a remarkable capacity to predict clinical outcomes with high sensitivity and specificity with the inclusion of just a few weekly clinical measurements. This degree of prediction accuracy after just 2 weeks of RT, will be critical to the potential utility of using this framework to inform treatment adaptation, as there are still 4-5 weeks of RT left in the treatment course for head and neck cancers. Additionally, the fact that this model forecasts outperform predictions based on simple volume reduction alone demonstrates the necessity of such a model for making high accuracy predictions early on in the treatment course.

The trend in $w_{n,optim}$ with the inclusion of increasing amounts of clinical measurements (FIG. 17) indicates that the forecasting method weights the patient-specific clinical measurements less in the first couple of weeks of RT and then begin weighing them 5-9 times more heavily than the information from the historic cohort for the remaining weeks. Notably, despite essentially ignoring the patient-specific measurements during the first few weeks of treatment, the forecasting method achieves high specificity. Additionally, even though the model was only trained to maximize predictive power for LRC, it performed well in accurately predicting DFS in both the training cohort and in the cross-validation cohort. It is conceivable that this may be due to these two outcomes being correlated[45].

The capacity of this method to accurately forecast clinical outcomes for individual patients has significant implications for clinical decision making. For example, this framework could be used to forecast and determine whether or not a patient will have a positive outcome from a course of RT mid-treatment. This may offer the first mathematical modeling-provided trigger to adjust RT based on individual patients' early response dynamics; to escalate radiation dose with or without concurrent therapies when necessary, or to de-escalate RT without sacrificing cure.

It should also be noted that neither the full version of the model nor the reduced version could capture large transient increases in tumor volume. Such large changes in volume may be due to factors not included in the model such as an influx of immune cells or increased fluid retention[46,47]. It may be possible to separate out these volumes if a different imaging modality, such as MRI, is used[48]. Of interest is that the early data points collected for test patients are weighted very low compared to historic training data. This further indicates that early transient radiographic response dynamics are not captured in the developed model and may, indeed, not be prognostic. The increased weight for individual patient data following week two during RT suggests that by that time radiation response dynamics are adequately captured in the presented model and highly predictive and prognostic.

Additionally, although the cross-validation was performed by learning $\lambda$ from one cohort and applying it as a pre-determined parameter in an independent cohort, more rigorous investigation and analysis is necessary to determine what degree of similarity (and by what metrics this should be determined) is needed between cohorts to transfer learned parameter values. This would include determining the minimum characteristics necessary to describe similar cohorts. If the model turns out to be insensitive to the value of $\lambda$ across multiple cohorts, then it may be possible for $\lambda$ to be set uniform for broader categories, possibly even other disease sites. It is interesting to note here that despite the cross-validation cohort having a maximum tumor volume at start of RT nearly two times larger than that of the training cohort, $\lambda$ was translatable between these cohorts. It should also be noted that although these cohorts were heterogeneous in terms of primary site of the cancer, there was no statistically discernible difference in outcome between the sites, due to the small number of local and distal failures.

There has been a recent proposal to utilize a genomic signature to stratify patients according to radiosensitivity[49]. It may be possible to find a comparable signature to predict $\delta$. However, as carrying capacity, and subsequently $\delta$, is an emergent property that is the sum of multiple factors, any biological signature to infer $\delta$ will likely need to include multiple components. This could include the degree of immune infiltration in the tumor microenvironment or what subtypes of immune cells make up the tumor-associated immune cells, which may be accessible by expression level sequencing data or analysis of stained tissue samples obtained as part of a pre-treatment biopsy or from surgical resection[50-52]. Depending on to what degree of confidence $\delta$ could be estimated from such pre-treatment information, this parameter estimate could potentially be integrated into the prediction pipeline with its own relative weight.

Supplemental Material and Methods

Parameter Optimization

Parameter optimization was performed using the particle swarm optimization function from the MATLAB Global Optimization Toolbox to search the $\lambda$-$\delta$ parameter space within the following bounds: $\lambda \in (0.055$ day$^{-1}$, $0.69$ day$^{-1}$) and $\delta \in (0,0.9)$. The upper bound for $\lambda$ was set as one cell division per day (ln 2), and the lower bound was calculated by a 92% cell loss factor with one cell division per day. (Matsu-ura T, Dovzhenok A, Aihara E, et al. Intercellular Coupling of the Cell Cycle and Circadian Clock in Adult Stem Cell Culture. *Mol Cell.* 2016; 64(5):900-912.) The optimizer was designed to find patient-specific values for each parameter, including cases in which either one or both of the parameters were constrained to be uniform across all patients. The optimization was performed 42 times with random starting points for the members of the swarm, in order to reach 95% probability that the optimizer was finding globally optimal results (FIG. 17). In all cases, only 1 or 2 optima were found. In the case that 2 optima were found, then the more frequently occurring parameter pair was selected.

Parameter Reduction Analysis

Model parameter reduction was accomplished by using a modified version of the optimization script described above to test setting $\lambda$, $\delta$, and both $\lambda$ and $\delta$ to be uniform across the entire cohort. The results of this comparison are detailed in Table 2. Both the Akaike Information Criterion and Bayesian Information Criterion were calculated to quantify the tradeoff of parameter reduction and goodness-of-fit of the reduced models. (Akaike H. A New Look at the Statistical Model Identification. *IEEE Trans Automat Contr.* 1974; 19(6):716-723; Schwarz G. Estimating the Dimension of a Model. *Ann Stat.* 1978; 6(2):461-464.) Notably, in both simplifications where $\lambda$ moved from a free parameter to a parameter that was uniform across the entire cohort there were minimal reductions in the goodness of fit ($\Delta R^2 < 0.025$), further supporting parameter insensitivity and setting $\lambda$ to a uniform value.

Calibration Forecasting

For the 38 training cohorts, the coefficients for equation 3 have mean$\pm$standard deviation values of $\beta_1 = -4.81 \times 10^{-7} \pm 6.83 \times 10^{-3}$ (weeks/cc)$^2$, $\delta_2 = 0.644 \pm 0.0561$ (weeks/cc), and $\beta_3 = -5.73 \times 10^4 \pm 9.15 \times 10^3$.

For the 38 training cohorts, the historical $\delta$-distribution had mean parameter values of $\mu_h = -3.53$ (corresponding to a median $\delta$ value of 0.0293) and $\sigma_h = 0.791$.

In order to find an optimal value for w for $n_{meas} = 1-4$, we performed a grid search across $w \in (0,10)$ with a step size of 0.1 to find the value of $w_n$ that maximized Youden's index in classifying LRC prediction for each leave-one-out training cohort. (Youden W J. Index for rating diagnostic tests. *Cancer.* 1950; 3(1):32-35.) This was done with 500 predictions as the analysis showed this to be sufficient for stable results despite the random sampling from the $\delta$-distribution (FIGS. 11A-11C). Across all of the cohorts, $w_{n,optim} < 2$ on average for $n_{meas} \leq 2$ and $w_{n,optim} > 2$ on average for $n_{meas} \geq 3$ (FIG. 17).

Volume Reduction Correlation and Informedness Comparison

Volume reduction as a prognostic feature was tested by calculating difference in volume from a given week of RT and before the first dose of RT for each patient. Thereafter, sensitivity and specificity values were calculated by sweeping over 100 possible volume reduction cutoffs to construct ROC curves for week of RT (FIG. 8B). Informedness was calculated using Youden's J-statistic (Youden W J. Index for rating diagnostic tests. *Cancer.* 1950; 3(1):32-35.), defined as follows:

$$J = \text{specificity} + \text{sensitivity} - 1$$

Single J-statistic values were calculated for volume reduction correlation for each week of RT and average J-statistic values from 10 simulations of 500 predictions each were used for evaluating the model predictions (FIG. 8C).

REFERENCES

1. Torres-Roca J F. A molecular assay of tumor radiosensitivity: a roadmap towards biology-based personalized radiation therapy. *Per Med.* 2012; 9(5):547-557. doi:10.2217/pme.12.55
2. Baskar R, Dai J, Wenlong N, Yeo R, Yeoh K-W. Biological response of cancer cells to radiation treatment. *Front Mol Biosci.* 2014; 1. doi:10.3389/fmolb.2014.00024
3. Harrison L B, Rishi A, Caudell J J, et al. The future of personalised radiotherapy for head and neck cancer. *Lancet Oncol.* 2017; 18(5):e266-e273. doi:10.1016/s1470-2045(17)30252-8
4. Enderling H, Alfonso J C L, Moros E, Caudell J J, Harrison L B. Integrating Mathematical Modeling into the Roadmap for Personalized Adaptive Radiation Therapy. *Trends in Cancer.* July 2019. doi:10.1016/J.TRECAN.2019.06.006
5. Aherne N J, Dhawan A, Scott J G, Enderling H. Mathematical oncology and it's application in non melanoma skin cancer—A primer for radiation oncology professionals. *Oral Oncol.* 2020; 103:104473.
6. Eschrich S, Zhang H, Zhao H, et al. Systems Biology Modeling of the Radiation Sensitivity Network: A Biomarker Discovery Platform. *Int J Radiat Oncol Biol Phys.* 2009; 75(2):497-505. doi:10.1016/j.ijrobp.2009.05.056
7. Eschrich S A, Pramana J, Zhang H, et al. A Gene Expression Model of Intrinsic Tumor Radiosensitivity: Prediction of Response and Prognosis After Chemoradiation. *Int J Radiat Oncol Biol Phys.* 2009; 75(2):489-496. doi:10.1016/j.ijrobp.2009.06.014
8. Eschrich S A, Fulp W J, Pawitan Y, et al. Validation of a radiosensitivity molecular signature in breast cancer. *Clin Cancer Res.* 2012; 18(18):5134-5143. doi:10.1158/1078-0432.CCR-12-0891
9. Fowler J F. How worthwhile are short schedules in radiotherapy?: A series of exploratory calculations. *Radiother Oncol.* 1990; 18(2):165-181.
10. Fowler J F. The linear-quadratic formula and progress in fractionated radiotherapy. *Br J Radiol.* 1989; 62(740):679-694. doi:10.1259/0007-1285-62-740-679
11. Brenner D J. The Linear-Quadratic Model Is an Appropriate Methodology for Determining Isoeffective Doses at Large Doses Per Fraction. *Semin Radiat Oncol.* 2008; 18(4):234-239. doi:10.1016/j.semradonc.2008.04.004
12. Sachs R K, Hlatky L R, Hahnfeldt P. Simple ODE models of tumor growth and anti-angiogenic or radiation treatment. *Math Comput Model.* 2001; 33(12-13):1297-1305. doi:10.1016/50895-7177(00)00316-2
13. Enderling H, Chaplain M A J, Hahnfeldt P. Quantitative modeling of tumor dynamics and radiotherapy. *Acta Biotheor.* 2010; 58(4):341-353.
14. Poleszczuk J, Krzywon A, Forys U, Widel M. Connecting Radiation-Induced Bystander Effects and Senescence to Improve Radiation Response Prediction. *Radiat Res.* 2015; 183(5):571-577. doi:10.1667/RR13907.1
15. Prokopiou S, Moros E G, Poleszczuk J, et al. A proliferation saturation index to predict radiation response and personalize radiotherapy fractionation. *Radiat Oncol.* 2015; 10(1):1-8. doi:10.1186/s13014-015-0465-x
16. Poleszczuk J, Walker R, Moros E G, Latifi K, Caudell J J, Enderling H. Predicting Patient-Specific Radiotherapy Protocols Based on Mathematical Model Choice for Proliferation Saturation Index. *Bull Math Biol.* 2018; 80(5):1195-1206. doi:10.1007/s11538-017-0279-0
17. Sunassee E D, Tan D, Ji N, et al. Proliferation Saturation Index in an adaptive Bayesian approach to predict patient-specific radiotherapy responses. *Int J Radiat Biol.* 2019; 95(10):1421-1426.
18. Anderson A R A, Quaranta V. Integrative mathematical oncology. *Nat Rev Cancer.* 2008; 8(3):227-234. doi:10.1038/nrc2329
19. Basanta D, Anderson A R A. Exploiting ecological principles to better understand cancer progression and treatment. *Interface Focus.* 2013; 3(4):20130020. doi:10.1098/rsfs.2013.0020
20. Gatenby R A, Vincent T L. Application of quantitative models from population biology and evolutionary game theory to tumor therapeutic strategies. *Mol Cancer Ther.* 2003; 2(9):919-927.
21. Gatenby R A, Brown J, Vincent T. Lessons from applied ecology: Cancer control using an evolutionary double bind. *Cancer Res.* 2009; 69(19):7499-7502. doi:10.1158/0008-5472.CAN-09-1354
22. Arnold K M, Flynn N J, Raben A, et al. The Impact of Radiation on the Tumor Microenvironment: Effect of Dose and Fractionation Schedules. *Cancer Growth Metastasis.* 2018; 11:117906441876163. doi:10.1177/1179064418761639
23. Demaria S, Ng B, Devitt M L, et al. Ionizing radiation inhibition of distant untreated tumors (abscopal effect) is immune mediated. *Int J Radiat Oncol Biol Phys.* 2004; 58(3):862-870. doi:10.1016/j.ijrobp.2003.09.012
24. Formenti S C, Demaria S. Systemic effects of local radiotherapy. *Lancet Oncol.* 2009; 10(7):718-726. doi:10.1016/51470-2045(09)70082-8
25. Formenti S C, Demaria S. Radiation therapy to convert the tumor into an in situ vaccine. *Int J Radiat Oncol Biol Phys.* 2012; 84(4):879-880. doi:10.1016/j.ijrobp.2012.06.020
26. Poleszczuk J T, Luddy K A, Prokopiou S, et al. Abscopal benefits of localized radiotherapy depend on activated T-cell trafficking and distribution between metastatic lesions. *Cancer Res.* 2016; 76(5):1009-1018. doi:10.1158/0008-5472.CAN-15-1423
27. López Alfonso J C, Poleszczuk J, Walker R, et al. Immunologic Consequences of Sequencing Cancer Radiotherapy and Surgery. *JCO Clin Cancer Informatics.* 2019; (3):1-16. doi:10.1200/cci.18.00075
28. Tozer G M, Myers R, Cunningham V J. Radiation-induced modification of blood flow distribution in a rat fibrosarcoma. *Int J Radiat Biol.* 1991; 60(1-2):327-334.
29. Friedman E J. Immune modulation by ionizing radiation and its implications for cancer immunotherapy. *Curr Pharm Des.* 2002; 8(19):1765-1780.
30. Matsu-ura T, Dovzhenok A, Aihara E, et al. Intercellular Coupling of the Cell Cycle and Circadian Clock in Adult Stem Cell Culture. *Mol Cell.* 2016; 64(5):900-912. doi:10.1016/j.molcel.2016.10.015

31. Stone M. Cross-validatory choice and assessment of statistical predictions. *J R Stat Soc Ser B.* 1974; 36(2): 111-133.
32. Moons K G M, Altman D G, Reitsma J B, et al. Transparent Reporting of a multivariable prediction model for Individual Prognosis or Diagnosis (TRIPOD): explanation and elaboration. *Ann Intern Med.* 2015; 162 (1):W1-W73.
33. Youden W J. Index for rating diagnostic tests. *Cancer.* 1950; 3(1):32-35.
34. Hahnfeldt P, Panigrahy D, Folkman J, Hlatky L. Tumor development under angiogenic signaling: A dynamical theory of tumor growth, treatment response, and postvascular dormancy. *Cancer Res.* 1999; 59(19):4770-4775. http://cancerres.aacrjournals.org/content/59/19/4770.short. Accessed Oct. 25, 2019.
35. Wilkie K P, Hahnfeldt P. Modeling the dichotomy of the immune response to cancer: cytotoxic effects and tumor-promoting inflammation. *Bull Math Biol.* 2017; 79(6): 1426-1448.
36. Wilkie K P, Hahnfeldt P. Tumor-immune dynamics regulated in the microenvironment inform the transient nature of immune-induced tumor dormancy. *Cancer Res.* 2013; 73(12):3534-3544.
37. Kareva I. Biological stoichiometry in tumor microenvironments. *PLoS One.* 2013; 8(1):e51844.
38. Chvetsov A V., Dong L, Palta J R, Amdur R J. Tumor-Volume Simulation During Radiotherapy for Head-and-Neck Cancer Using a Four-Level Cell Population Model. *Int J Radiat Oncol Biol Phys.* 2009; 75(2):595-602. doi:10.1016/j.ijrobp.2009.04.007
39. Chvetsov A V., Yartsev S, Schwartz J L, Mayr N. Assessment of interpatient heterogeneity in tumor radiosensitivity for nonsmall cell lung cancer using tumor-volume variation data. *Med Phys.* 2014; 41(6). doi: 10.1118/1.4875686
40. Lewin T D, Byrne H M, Maini P K, Caudell J J, Moros E G, Enderling H. The importance of dead material within a tumour on the dynamics in response to radiotherapy. *Phys Med Biol.* 2020; 65(1):15007.
41. Chvetsov A V, Sandison G A, Schwartz J L, Rengan R. Ill-posed problem and regularization in reconstruction of radiobiological parameters from serial tumor imaging data. *Phys Med Biol.* 2015; 60(21):8491.
42. Laird A K. Dynamics of tumour growth: comparison of growth rates and extrapolation of growth curve to one cell. *Br J Cancer.* 1965; 19(2):278.
43. Steel G G, Lamerton L F. The growth rate of human tumours. *Br J Cancer.* 1966; 20(1):74.
44. Fournier D V, Weber E, Hoeffken W, Bauer M, Kubli F, Barth V. Growth rate of 147 mammary carcinomas. *Cancer.* 1980; 45(8):2198-2207.
45. Michiels S, Le Ma\^\itre A, Buyse M, et al. Surrogate endpoints for overall survival in locally advanced head and neck cancer: meta-analyses of individual patient data. *Lancet Oncol.* 2009; 10(4):341-350.
46. Lugade A A, Moran J P, Gerber S A, Rose R C, Frelinger J G, Lord E M. Local radiation therapy of B16 melanoma tumors increases the generation of tumor antigen-specific effector cells that traffic to the tumor. *J Immunol.* 2005; 174(12):7516-7523.
47. Bae J S, Roh J-L, Lee S, et al. Laryngeal edema after radiotherapy in patients with squamous cell carcinomas of the larynx and hypopharynx. *Oral Oncol.* 2012; 48(9): 853-858.
48. Jardim-Perassi B V, Huang S, Dominguez-Viqueira W, et al. Multiparametric MRI and Coregistered Histology Identify Tumor Habitats in Breast Cancer Mouse Models. *Cancer Res.* 2019; 79(15):3952-3964.
49. Mellon E, Yue B, Strom T S, et al. A genome-based model for adjusting radiotherapy dose (GARD): a retrospective, cohort-based study. *Lancet Oncol.* 2016; 18(2): 202-211. doi:10.1016/51470-2045(16)30648-9
50. Thorsson V, Gibbs D L, Brown S D, et al. The Immune Landscape of Cancer. *Immunity.* 2018; 48(4):812-830.e14. doi:10.1016/J.IMMUNI.2018.03.023
51. Daniel Grass G, Alfonso J C L, Welsh E, et al. Harnessing tumor immune ecosystem dynamics to personalize radiotherapy. bioRxiv. January 2020:2020.02.11.944512. doi:10.1101/2020.02.11.944512
52. Brady R, Enderling H. Mathematical Models of Cancer: When to Predict Novel Therapies, and When Not to. *Bull Math Biol.* 2019; 81(10):3722-3731.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method, comprising:
receiving at least two images of a target patient's tumor including a first image captured at a first time point and a second image captured at a second time point;
deriving respective values for tumor volume of the target patient's tumor at the first time point and the second time point from the at least two images;
calculating a change in tumor volume between the first and second time points based on the respective values for tumor volume;
estimating a patient-specific carrying capacity based on a logistic growth model and the change in tumor volume between the first and second time points;
predicting a volume of the target patient's tumor at a future time point during radiation treatment based, at least in part, on a historical carrying capacity reduction fraction distribution and the patient-specific carrying capacity; and
predicting a patient-specific outcome of radiation therapy for the target patient based, at least in part, on the predicted volume of the target patient's tumor at the future time point.

2. The method of claim 1, wherein the first point in time is prior to a beginning of radiation therapy.

3. The method of claim 1, wherein the second point in time is at a beginning of radiation treatment.

4. The method of claim 1, further comprising:
receiving a respective value for tumor volume of the target patient's tumor at a third time point;
calculating a change in tumor volume between the second and third time points based on the respective values for tumor volume;
estimating a patient-specific carrying capacity reduction fraction based on the logistic growth model and the change in tumor volume between the second and third time points; and
predicting the volume of the target patient's tumor at the future time point during radiation treatment based, at least in part, on the patient-specific carrying capacity reduction fraction and the change in tumor volume between the second and third time points, wherein the third time point is during administration of radiation treatment.

5. The method of claim 4, wherein the third time point is at a second, third, fourth, or fifth week of radiation treatment.

6. The method of claim 4, wherein the future time point is at a sixth week of radiation treatment.

7. The method of claim 4, wherein the step of predicting the volume of the target patient's tumor at the future time point in radiation treatment based, at least in part, on the patient-specific carrying capacity reduction fraction and the change in tumor volume between the second and third time points comprises:
updating the historical carrying capacity reduction fraction distribution to include the patient-specific carrying capacity reduction fraction for the target patient;
randomly sampling from the updated historical carrying capacity reduction fraction distribution; and
simulating tumor volume dynamics during radiation treatment for the target patient.

8. The method of claim 4, further comprising weighting the patient-specific carrying capacity reduction fraction for the target patient.

9. The method of claim 1, wherein the patient-specific outcome is predicted by comparing a change in tumor volume at the future time point to a threshold.

10. The method of claim 1, wherein the predicted patient-specific outcome is one of: i) a percentage chance of success of radiation therapy, ii) locoregional control (LRC), or iii) disease-free survival (DFS).

11. The method of claim 1, further comprising at least one of: i) treating the target patient based on the predicted patient-specific outcome or ii) administering radiation treatment after the second time point.

12. A system, comprising:
a processor; and
a memory operably coupled to the processor, the memory having computer-executable instructions stored thereon that, when executed by the processor, cause the processor to:
receiving at least two images of a target patient's tumor including a first image captured at a first time point and a second image captured at a second time point;
derive respective values for tumor volume of the target patient's tumor at the first time point and the second time point;
calculate a change in tumor volume between the first and second time points based on the respective values for tumor volume;
estimate a patient-specific carrying capacity based on a logistic growth model and the change in tumor volume between the first and second time points;
predict a volume of the target patient's tumor at a future time point during radiation treatment based, at least in part, on a historical carrying capacity reduction fraction distribution and the patient-specific carrying capacity; and
predict a patient-specific outcome of radiation therapy for the target patient based, at least in part, on the predicted volume of the target patient's tumor at the future time point.

13. The system of claim 12, wherein the memory has further computer-executable instructions stored thereon that, when executed by the processor, cause the processor to:
receive a respective value for tumor volume of the target patient's tumor at a third time point;
calculate a change in tumor volume between the second and third time points based on the respective values for tumor volume;
estimate a patient-specific carrying capacity reduction fraction based on the logistic growth model and the change in tumor volume between the second and third time points; and
predict the volume of the target patient's tumor at the future time point during radiation treatment based, at least in part, on the patient-specific carrying capacity reduction fraction and the change in tumor volume between the second and third time points, wherein the third time point is during administration of radiation treatment.

14. The system of claim 13, wherein the third time point is at a second, third, fourth, or fifth week of radiation treatment.

15. The system of claim 13, wherein the future time point is at a sixth week of radiation treatment.

16. The system of claim 13, wherein the step of predicting the volume of the target patient's tumor at the future time point in radiation treatment based, at least in part, on the patient-specific carrying capacity reduction fraction and the change in tumor volume between the second and third time points comprises:
updating the historical carrying capacity reduction fraction distribution to include the patient-specific carrying capacity reduction fraction for the target patient;
randomly sampling from the updated historical carrying capacity reduction fraction distribution; and
simulating tumor volume dynamics during radiation treatment for the target patient.

17. The system of claim 13, wherein the memory has further computer-executable instructions stored thereon that, when executed by the processor, cause the processor to weight the patient-specific carrying capacity reduction fraction for the target patient.

18. The system of claim 12, wherein the at least two images are computed-tomography (CT) images or magnetic resonance images (MRI).

* * * * *